United States Patent
Benin et al.

(10) Patent No.: US 11,116,857 B1
(45) Date of Patent: Sep. 14, 2021

(54) APPARATUS AND METHOD FOR TOUCHLESS SANITATION OF HANDHELD OBJECTS

(71) Applicant: 11958267 Canada Inc., Waterloo (CA)

(72) Inventors: Ronen Benin, Waterloo (CA); Gordon Evans, Waterloo (CA)

(73) Assignee: 11958267 Canada Inc., Waterloo (CA)

( * ) Notice: Subject to any disclaimer, the term of this patent is extended or adjusted under 35 U.S.C. 154(b) by 0 days.

(21) Appl. No.: 17/025,601

(22) Filed: Sep. 18, 2020

Related U.S. Application Data

(60) Provisional application No. 63/016,150, filed on Apr. 27, 2020.

(51) Int. Cl.
*A61L 2/10* (2006.01)
*A61L 2/24* (2006.01)

(52) U.S. Cl.
CPC ...... *A61L 2/10* (2013.01); *A61L 2/24* (2013.01); *A61L 2202/11* (2013.01); *A61L 2202/121* (2013.01); *A61L 2202/122* (2013.01); *A61L 2202/123* (2013.01); *A61L 2202/14* (2013.01)

(58) Field of Classification Search
CPC .......... A61L 2/10; A61L 2/24; A61L 2202/11
See application file for complete search history.

(56) References Cited

U.S. PATENT DOCUMENTS

| | | | |
|---|---|---|---|
| 8,058,629 B2 * | 11/2011 | Long | A61L 2/10 250/455.11 |
| 8,296,493 B1 | 10/2012 | Engelhardt et al. | |
| 8,606,981 B2 | 12/2013 | Engelhardt et al. | |
| 8,977,796 B2 | 3/2015 | Engelhardt et al. | |
| 9,254,342 B2 | 2/2016 | Engelhardt et al. | |
| 10,166,308 B2 | 1/2019 | Engelhardt et al. | |
| 10,583,213 B2 | 3/2020 | Stibich et al. | |
| 2010/0044582 A1 * | 2/2010 | Cooper | A61L 2/24 250/455.11 |
| 2016/0101202 A1 * | 4/2016 | Gil | A61L 2/202 422/186.3 |
| 2019/0151490 A1 * | 5/2019 | Murrell | A61L 2/22 |
| 2020/0353111 A1 * | 11/2020 | Schmiddem | A47K 17/00 |

* cited by examiner

*Primary Examiner* — Kevin Joyner
(74) *Attorney, Agent, or Firm* — Own Innovation; James W. Hinton

(57) ABSTRACT

A sanitizer apparatus and method for touchless sanitation of handheld objects such as mobile devices using ultraviolet radiation is provided. The sanitizer is configured for touchless operation to prevent cross contamination from a user physically touching the sanitizer. The sanitizer includes one or more UV radiation sources for exposing all external surfaces of the object being sanitized to UV-C radiation. A platform moves the object to be sanitized past the UV radiation sources and the interior of the sanitizer is reflective to ensure all external surfaces of the object receive the requisite dosage of UV-C radiation to inactivate microorganisms. The sanitizer includes one or more doors for restricting access to the interior of the sanitizer and preventing UV radiation from escaping the interior when the doors are closed. The sanitizer includes safety features to prevent the UV radiation sources from being switched on while the doors are open.

15 Claims, 23 Drawing Sheets

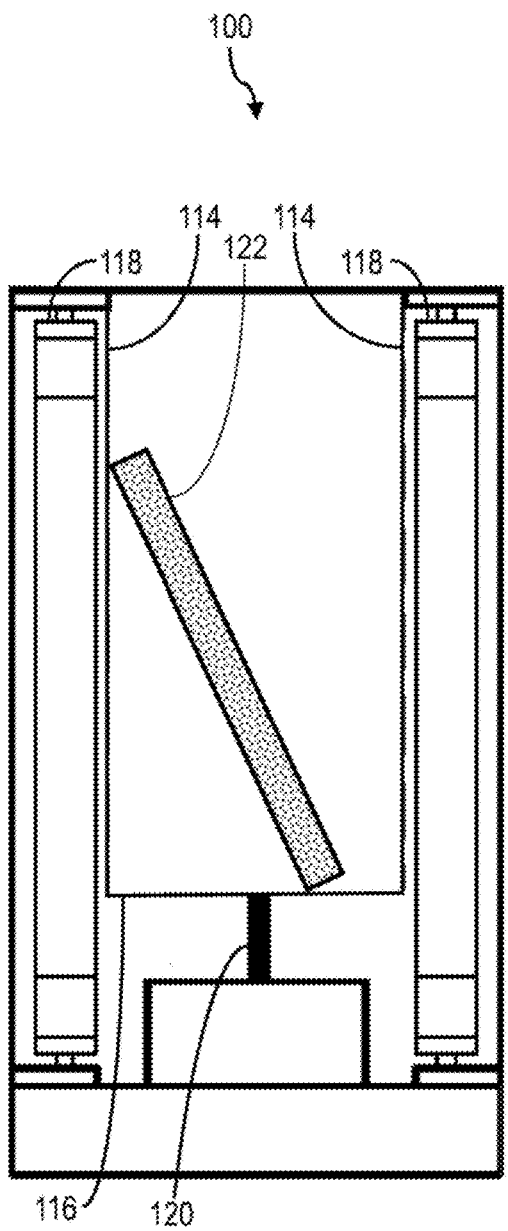
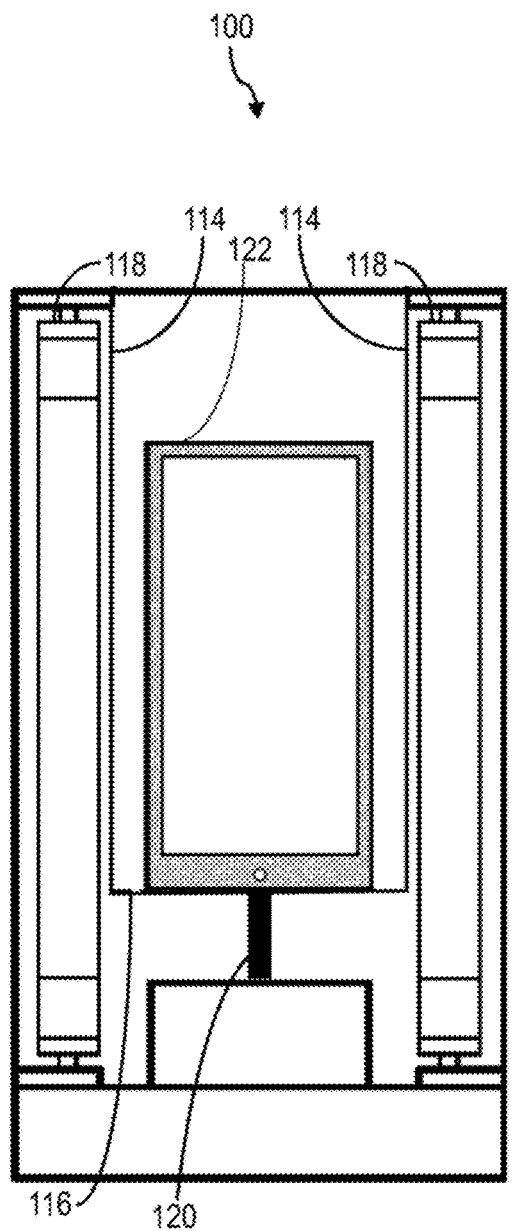
FIG. 1F
FIG. 1G

APPARATUS AND METHOD FOR TOUCHLESS SANITATION OF HANDHELD OBJECTS

TECHNICAL FIELD

The embodiments disclosed herein relate to apparatus for sanitation and sterilization, and, in particular to an apparatus and method for touchless sanitation of handheld objects such as portable electronic devices.

INTRODUCTION

Portable electronic devices including mobile phones (i.e. smartphones) and tablets have become ubiquitous in everyday life. Portable electronic devices are employed for personal use, completing work tasks, and communication. Often a user will use a single portable electronic device for personal and work use. Even when a user has separate devices for personal and work use, often they will carry both devices, at the same time, when at work.

Maintaining cleanliness and sanitary/sterile conditions is essential in healthcare, biological research, agriculture, food/hospitality and other industries. This is especially true during "flu-season" or during a pandemic when viral or bacterial-transmitted disease is spreading among a population. Thus, for workers in industries where sanitary/sterile conditions must be maintained, there is an issue of how to effectively sanitize portable electronic devices, and other handheld objects such as keys, whether for personal or work usage when entering/exiting a workplace or premises where sanitary conditions are maintained (e.g. a quarantine ward at a hospital).

Ultraviolet germicidal irradiation is a well-known technique for disinfection and sanitation using ultraviolet (UV) radiation, to inactivate microorganisms. In particular, short wave ultraviolet C (UV-C) radiation between 254 nm and 275 nm is known as for being the range most effective for breaking down the chemical bonds of nucleic acid, thereby preventing DNA/RNA replication and rendering microorganisms unable to reproduce. Short wave UV-C radiation between 200 nm and 250 nm, is also known to break down organic carbon-based molecules further contributing to disabling microorganisms. Ultraviolet A, ultraviolet B and other forms of ultraviolet light do not share the germicidal characteristics of UV-C radiation.

Existing sanitizers employ UV-C radiation for germicidal and disinfecting purposes, however these sanitizers are not designed specifically for disinfecting smaller handheld objects, and as such are often large/bulky, require significant energy input and cannot be installed at multiple easy-to-access locations, for example, the entrance/exit to a hospital staff dressing room.

Even sanitizers specifically designed for portable electronic devices have the limitations of long sanitation times (several minutes), and require the user to physically touch the sanitizer to set the operating conditions and/or when inserting and removing the device from the sanitizer. As such, the physical contact with the sanitizer increases the chance of cross-contamination between the external surfaces of the sanitizer and the electronic device and the user. A further risk is the user may be exposed to UV radiation that "leaks" out of the sanitizer during sanitation.

Accordingly, there is a need for a sanitizer specifically for handheld objects including portable electronic devices that can be operated in a touchless manner, has quick disinfection times, prevents user exposure to UV radiation and is in a small, convenient to use form factor.

SUMMARY

According to an embodiment, there is a method for touchless sanitation of handheld objects comprising: detecting an object to be sanitized; moving the object into a chamber of a sanitizer; closing the chamber, such that no UV radiation can escape the chamber; exposing all external surfaces of the object to UV-C radiation; and moving the object out of the chamber, whereby the object may be picked up by a user without touching any part of the sanitizer.

According to some embodiments, the method further comprises: receiving a touchless signal to use the sanitizer; and providing access to the chamber of the sanitizer. According to some embodiments, the method further comprises ending access to the chamber of the sanitizer. According to some embodiments, receiving a touchless signal comprises one of: receiving an infrared signal by an infrared sensor; receiving a thermal infrared signal from body heat by a thermal infrared sensor; receiving a signal from a load sensor; receiving a signal from a proximity sensor; receiving a radio frequency identification (RFID) signal by a RFID receiver; or receiving a near field communication (NFC) signal by a NFC receiver.

According to some embodiments, there is a touchless sanitizer for handheld objects. The sanitizer comprises: a housing having an opening; a chamber within the housing for receiving an object to be sanitized, wherein the chamber is adjacent to the opening; a platform, wherein the platform is movable within the chamber between a first position and a second position; at least one door for covering the opening and restricting access to the chamber, wherein the door is moveable between an open position and a closed position; one or more ultraviolet radiation sources within the housing and positioned around the chamber, whereby at least a portion of the chamber can be directly irradiated by the ultraviolet radiation sources; and an actuator connected to the platform and the door, for moving the platform between the first position and the second position, whereby the movement of the platform may be mechanically coupled to the movement of the door.

According to some embodiments, the door being in the closed position is mechanically coupled to the platform being in the second position. According to some embodiments, the door being in the open position is mechanically coupled to the platform being in the second position. According to some embodiments, the door forms an end of the platform.

According to some embodiments, the sanitizer further comprises a detector disposed on an external surface of the sanitizer for receiving a touchless signal. According to some embodiments the detector is one of: an infrared sensor, a thermal infrared sensor, a load sensor/switch, a proximity sensor, a RFID receiver or a NFC receiver.

According to some embodiments, the platform and the chamber are constructed of a material transmissive to UV radiation, for example, quartz glass. According to some embodiments, the UV radiation sources are UV lamps or LEDs. According to some embodiments, the interior of the housing is reflective to UV-C radiation. According to some embodiments, the housing and the door prevent the release of UV radiation from the sanitizer.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings:

FIG. 1F is the sanitizer of FIG. 1B showing a portable device within the sanitizer;

FIG. 1G is a side cross-sectional view through section B-B of the sanitizer shown in FIG. 1A showing a portable device within the sanitizer;

DETAILED DESCRIPTION

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

References herein to ultraviolet ("UV") radiation refers to ultraviolet radiation encompassing ultraviolet A, ultraviolet B and ultraviolet C radiation. References herein to ultraviolet C ("UV-C") radiation means "short wave" UV-C radiation between 200 nm to 280 nm.

Figure 1A:
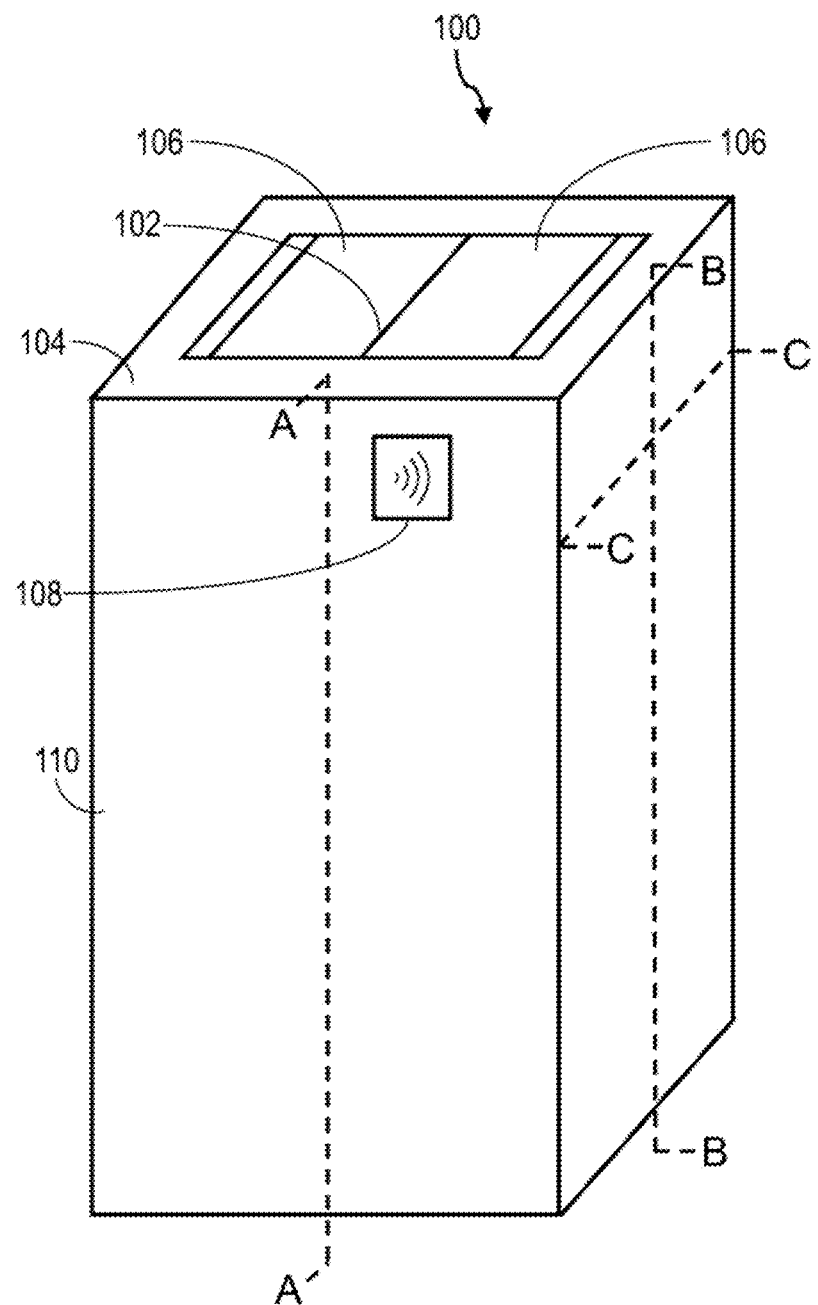
FIG. 1A is a perspective view of a sanitizer, according to an embodiment.

Referring to FIG. 1A, illustrated therein is a sanitizer 100, according to an embodiment. The sanitizer 100 includes an opening 102 in a top wall 104 of the sanitizer 100. The opening 102 is large enough to allow an object to be sanitized such as a portable electronic device (i.e. a smartphone or tablet) or other handheld objects (e.g. headphones, or a wallet) to pass through the opening 102 into the sanitizer 100. The opening 102 is covered by two moveable doors 106. According to some embodiments, the opening 102 may be covered by a single door 106. According to other embodiments, the opening 102 and the door 106 may be on an external surface 110 of the sanitizer 100.

The sanitizer 100 may include a button, lever or other means of activating a "self-cleaning mode" on one of the surfaces of the machine. The sanitizer 100 may have inside components, including the underside of the doors 106, made of a variety of materials, such as plastic, and painted, constructed of, or covered with a reflective coating, such as Teflon, aluminum or chrome.

The sanitizer 100 includes a detector 108 on the external surface 110 of the sanitizer 100 for detecting the presence of a user or a portable electronic device. The detector 108 may be an infrared sensor, a proximity sensor, a load sensor/switch, a radio-frequency identification (RFID) receiver or other near-field communication (NFC) receiver. According to an embodiment, the detector 108, may be an NFC receiver for touchless secure payment systems. The detector 108 is operably connected to the doors 106, whereby when the detector 108 detects a user/electronic device, the doors 106 open allowing access to an interior chamber of the sanitizer 100 via the opening 102. According to an embodiment, the external surface 110 may be the top wall 104. The doors 106 may come in different shapes or sizes (singular, dual, or none at all. Some embodiments may have an electable tray where the end piece of the tray acts as a door when reinserted.)

The device may have its entry "doors" on the top or any one of the sides.

The relatively small form factor of the sanitizer 100 allows the sanitizer 100 to be installed and used in an unobtrusive manner in a variety of locations throughout a workplace. For example, the sanitizer 100 may be placed on a table or countertop. The sanitizer 100 may be mounted to a wall. The sanitizer 100 may be located on the exterior of a building and constructed with appropriate weather-proofed materials.

Figure 1B:
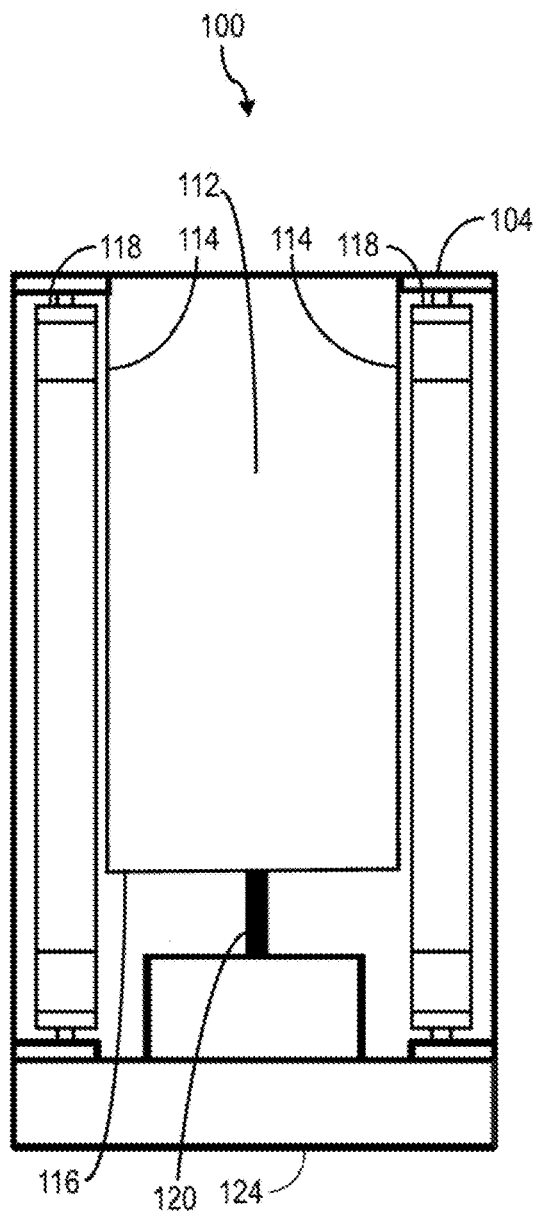
FIG. 1B is a side cross-sectional view through section A-A of the sanitizer shown in FIG. 1A.
Figure 1C:
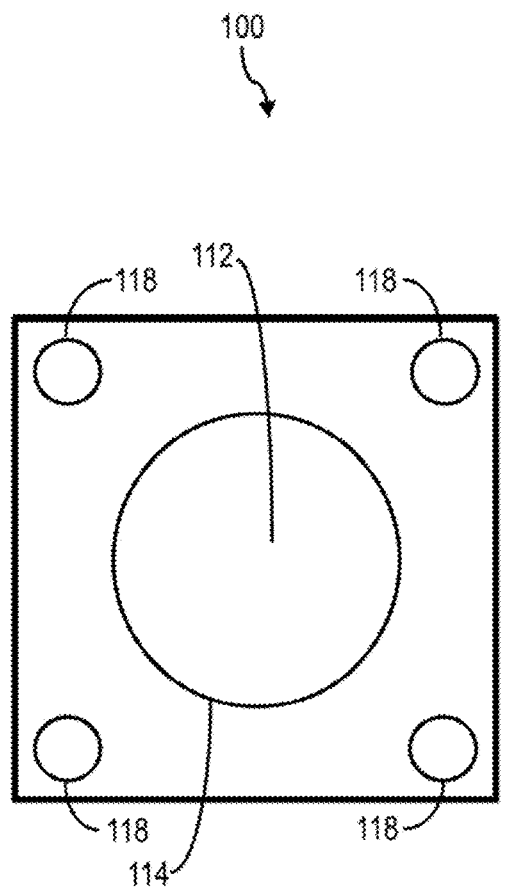
FIG. 1C is a top cross-sectional view through section C-C of the sanitizer shown in FIG. 1A.

Referring to FIGS. 1B and 1C, illustrated therein are a side cross-sectional view through section A-A (FIG. 1B) and a top cross-sectional view through section C-C (FIG. 1C) of the sanitizer 100 shown in FIG. 1A. The sanitizer 100 includes a chamber 112 for receiving a portable electronic device (not shown). The chamber 112 is substantially cylindrical in shape, and is bounded by a circular wall 114 and a moveable platform 116. According to other embodiments, the chamber 112 may be substantially rectangular or cuboid in shape. In variants the moveable platform may be a conveyor or a holster configured to hold the electronic device. The chamber and/or the tube/tray that enters and exits the machine may in this shape and may be constructed of quartz glass or materials with similar UV transmittance qualities.

The circular wall 114 and platform 116 are constructed of a transparent material that has high transmittance to UV radiation, preferably quartz glass having a thickness of ~3 mm. It is preferable to use quartz for the circular wall 114 and platform 116 since quartz has near ~100% transmissivity to UV radiation, compared to other types of glass or transparent polymers which may reflect or absorb UV radiation.

The sanitizer 100 includes a plurality of UV light sources 118 for illuminating the chamber 112 with UV light. The UV light sources 118 are preferably UV lamps 118, for example, Philips TUV PL-S. As shown, the sanitizer 100 includes four UV lamps 118 positioned around the chamber 112, such that the entire chamber 112 is illuminated directly by incident UV radiation, with no "blind spots." This is advantageous compared to existing systems which use LEDs as the source of UV radiation which can lead to non-uniform illumination of all the external surfaces of an object leading to non-uniform sanitation of the object. According to other embodiments, the sanitizer 100 may include more or less than four UV lamps 118, so long as the entire chamber 112 is illuminated directly by incident UV radiation.

The sanitizer 100 may include reflectors (not shown) to further direct/concentrate the UV radiation to the chamber 112. For example, the interior of the sanitizer 100, including the underside of the doors 106, may be coated with reflective paint, or may be made of reflective materials, to direct/concentrate the UV radiation to the chamber 112.

Now referring to FIG. 1B, the sanitizer 100 includes an actuator 120 connected to the platform 116 for vertically (or horizontally, depending on the orientation of the sanitizer 100) moving the platform 116. The actuator 120 may be an electromechanical actuator 120, for example, a rack and pinion operatively connected to a motor, for raising and lowering the platform 116. The actuator 120 may be a linear motor-screw actuator or a belt-driven actuator for linear motion. According to embodiments wherein the opening (i.e. opening 102 in FIG. 1A) is in an external surface (i.e. external surface 110 in FIG. 1A) rather than the top surface 104 of the sanitizer 100, the actuator 120 may be configured to move the platform horizontally.

Still referring to FIG. 1B, the sanitizer 100 includes a base 124. The base 124 includes an electronic circuit (not shown), including a computer processor operably coupled to a memory for storing processor-executable instructions. When executed by the processor, the instructions govern the operation of the UV lamps 118 and the actuator 120 (and by extension the movement of the platform 116 and doors 106). Thus, the sanitizer 100 is pre-programmed with the instructions for automated operation without the need for the user to input settings. This is advantageous in preventing potential cross-contamination caused by users touching the sanitizer 100.

The base 124 includes one or more rechargeable or replaceable batteries (not shown) for powering the UV lamps 118 and the actuator 120. According to some embodiments the base 124 includes electrical components for connecting the sanitizer 100 to an AC power source (e.g. a power socket).

Figure 1D:
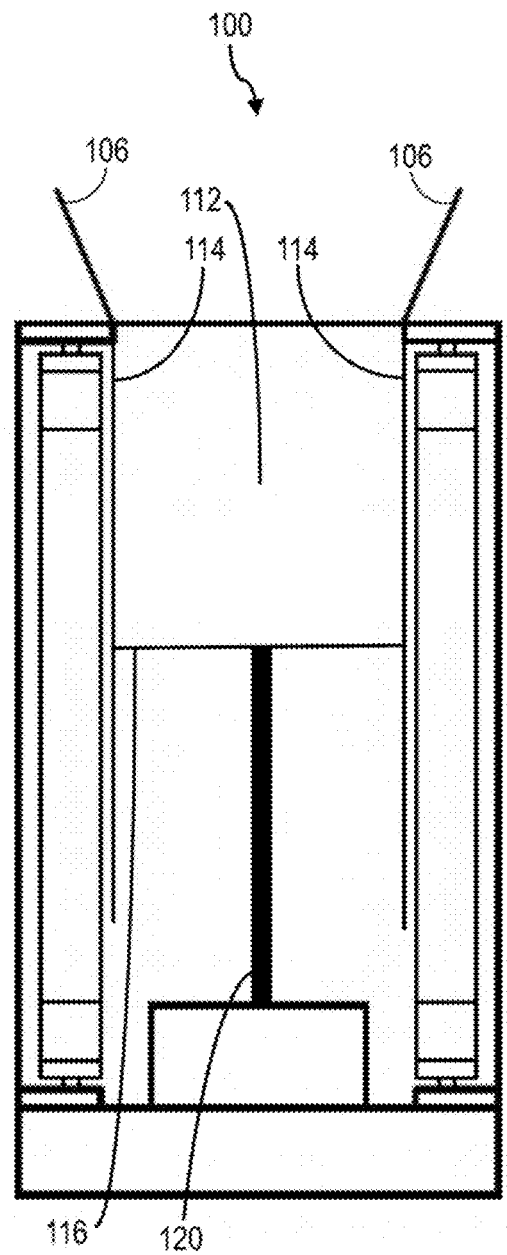
FIG. 1D is the sanitizer of FIG. 1B shown in a configuration for receiving an object to be sanitized.

Referring to FIG. 1D, illustrated therein is the sanitizer 100 of FIG. 1B shown in a configuration for receiving an object to be sanitized. The circular wall 114 is immovably attached to the top wall 104. The platform 116 is vertically moveable, by the actuator 120, within the space enclosed by the circular wall 114. The actuator 120 may be operatively connected to the doors 106, for example by use of levered or telescoping arms (not shown). The movement of the platform 116 by the actuator 120 is mechanically coupled to the opening/closing of the doors 106. For example, the actuator 120 moving the platform 116 upwards will cause the doors 106 to open. Conversely, the actuator 120 moving the platform 116 downward will cause the doors 106 to close.

Figure 3A:
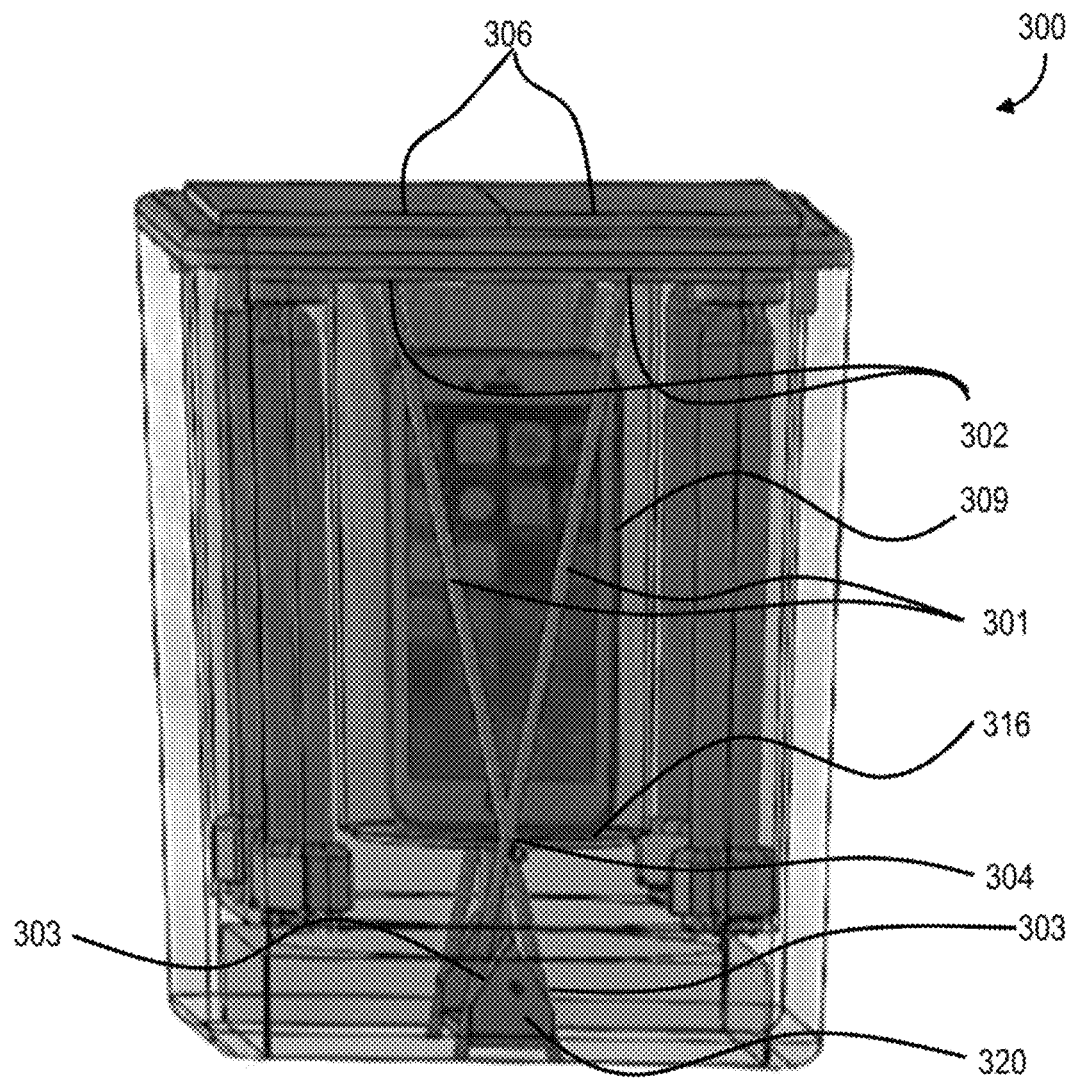
FIGS. 3A-3C are perspective views of a sanitizer for sanitizing an object, in a closed position (FIG. 3A), an intermediate position (FIG. 3B), and an open position (FIG. 3C), in accordance with an embodiment.
Figure 3B:
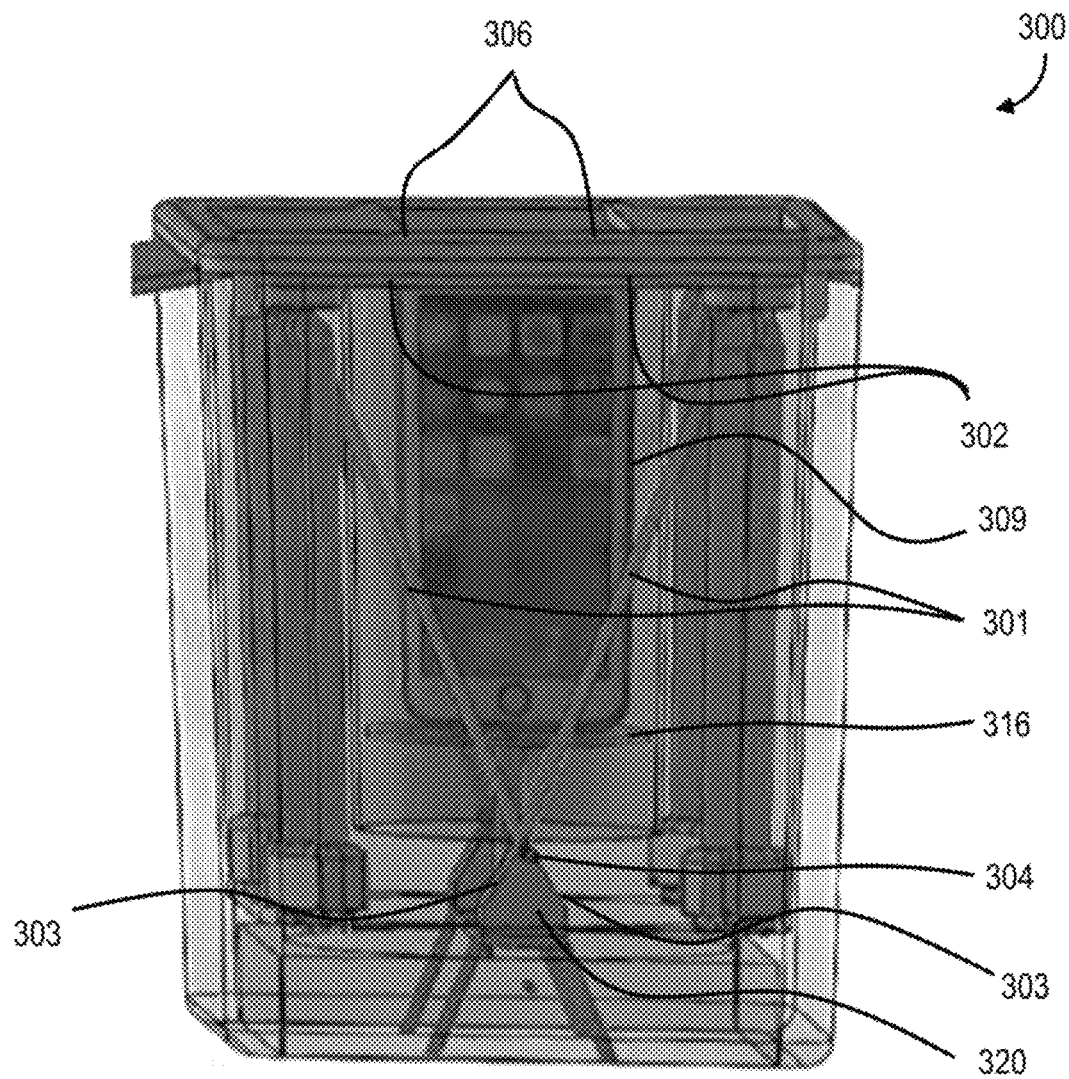
Figure 3C:
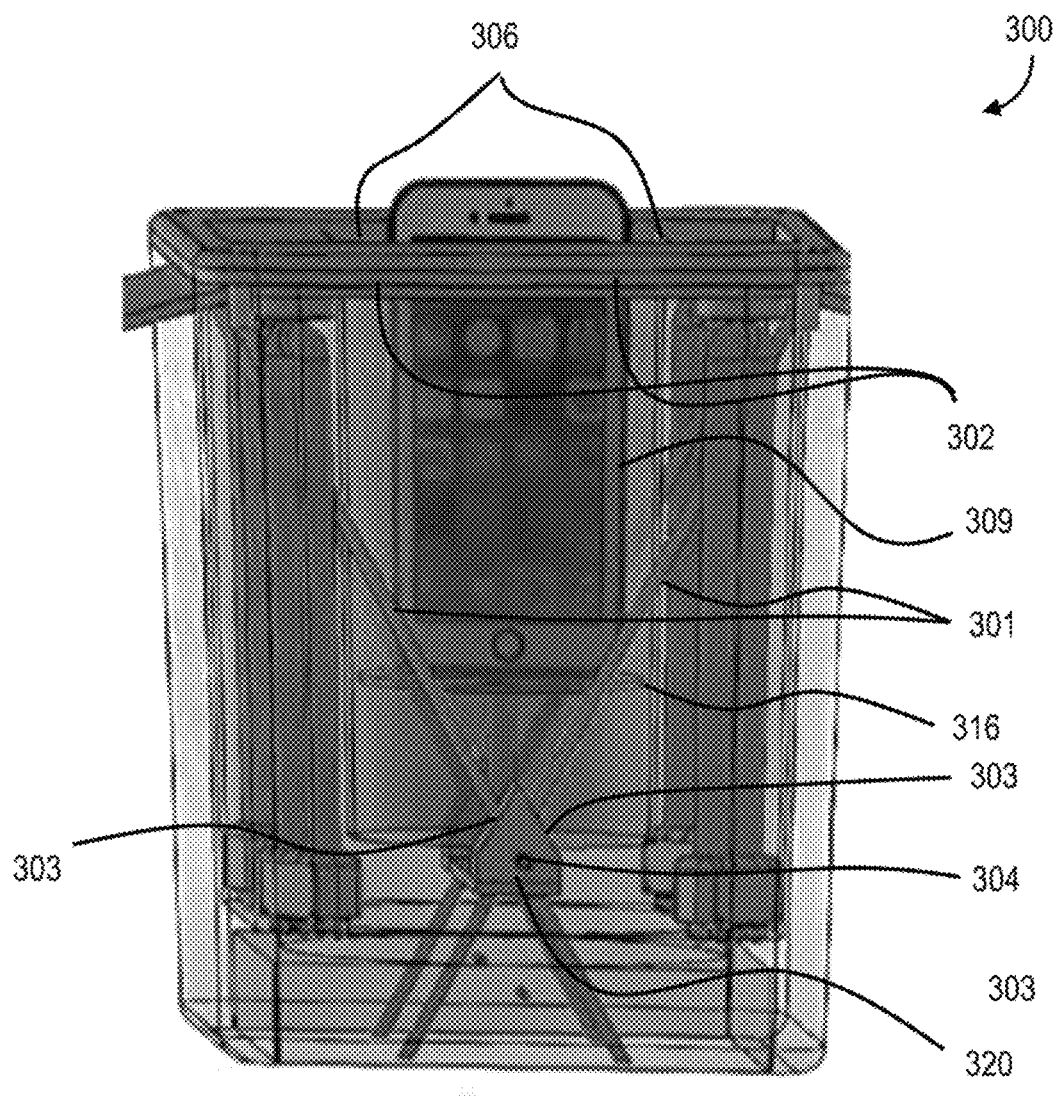

Turning to FIGS. 3A-3C, illustrated there in is a sanitizer 300 for sanitizing an object 309, such as a mobile device, in a closed position (FIG. 3A), an intermediate position (FIG. 3B), and an open position (FIG. 3C), in accordance with a further embodiment. The sanitizer 300 includes a platform 316 that is mechanically coupled to doors 306 by a pair of scissor arms 301. A first end 302 of each arm is attached to the doors 306. A second end 303 of each arm 301 is engaged by an actuator 320. To open the doors 306, the actuator 320 exerts a force on the second ends 303 of the arms thereby causing the scissor arms to pivot about pivot hinge 304 causing the first ends 302 of the arms to open the doors 306. The fulcrum of each scissor arm is positioned on a common axis at the pivot hinge 304, such that the scissor arms 302 are biased to maintain the doors 306 in the closed position until the actuator 320 engages the second ends 303 of the arms to move the doors 306 to the open position (FIG. 3C). When the actuator 320 disengages from the second ends 303, the doors 306 return to the closed position (FIG. 3A).

Referring again to FIG. 1E, illustrated therein is the sanitizer 100 of FIG. 1D shown in relation to a portable device 122. When the doors 106 are opened and the platform 116 is raised, an object to be sanitized (i.e. the portable device 122) may be placed on the platform 116. The platform 116 may include a load sensor (not shown) for detecting when the portable device 122 is placed on the platform 116. Upon detecting an object on the platform 116, the actuator 120 is configured to lower the platform 116 and close the doors 106. The sanitizer 100 may include a thermal infrared detector (not shown) positioned adjacent to the doors 106 to detect whether a user's hand is within the chamber 112 (i.e. between the doors 106) and prevent the doors 106 from closing.

Figure 1E:
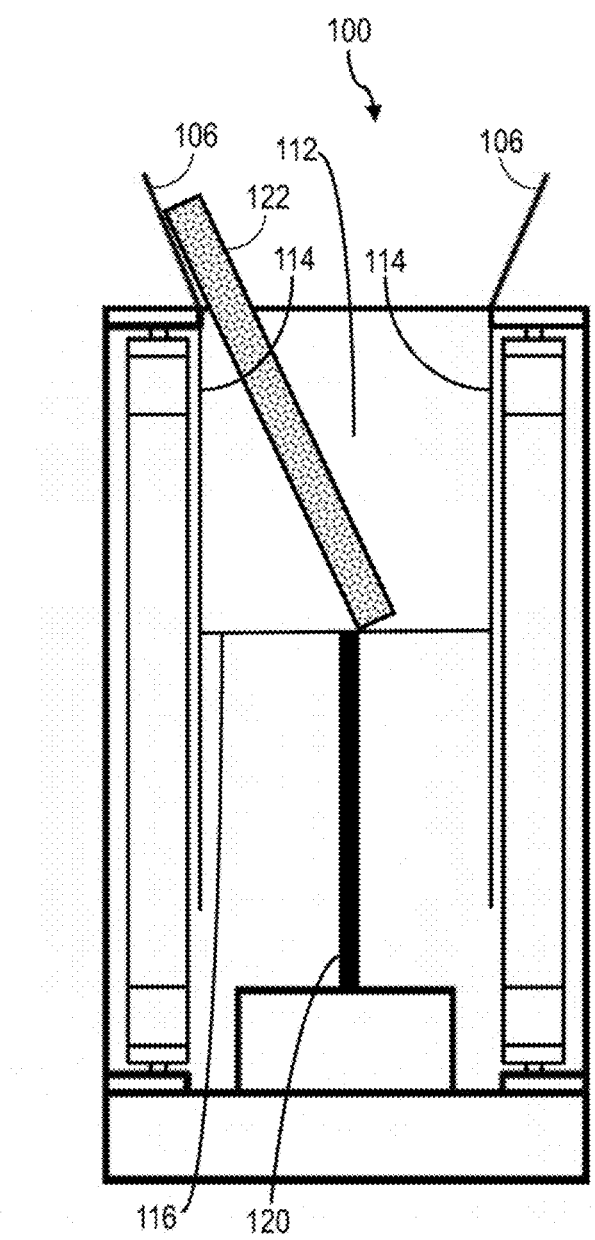
FIG. 1E is the sanitizer of FIG. 1D shown in relation to a portable device inserting into the sanitizer.
Figure 1H:
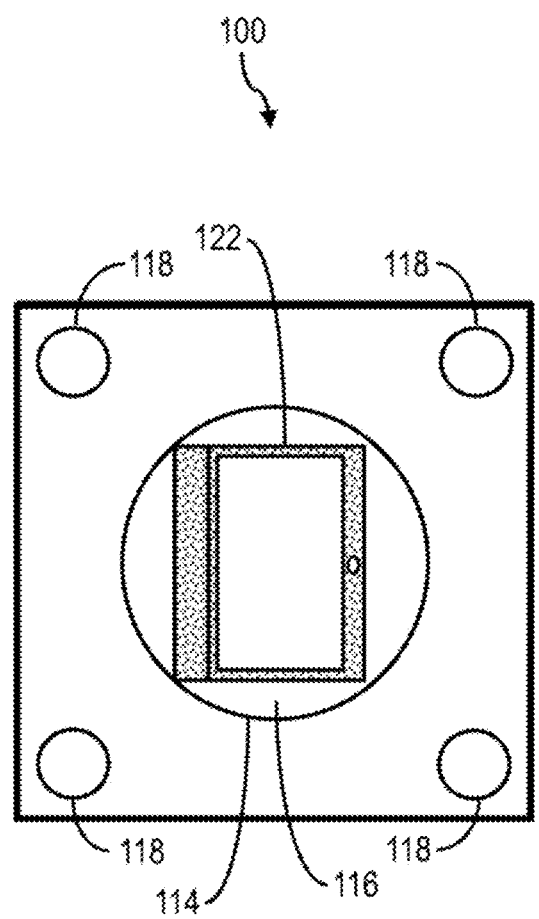
FIG. 1H is a top cross-sectional view through section C-C of the sanitizer shown in FIG. 1A and showing a portable device within in the sanitizer.

Referring to FIGS. 1F-1H, illustrated therein are a side cross-sectional view through section A-A of FIG. 1A (FIG. 1F), a side cross-sectional view through section B-B of FIG. 1A (FIG. 1G), and a top cross-sectional view through section C-C of FIG. 1A (FIG. 1H) showing a portable device 122 within the sanitizer 100. The portable device 122 is positioned on the platform 116 such that all external surfaces of the portable device 122 are directly exposed to UV radiation from the UV lamps 118. For example, as shown in FIG. 1F, the portable device 122 is tilted to rest against the circular wall 114. This allows for all sides of the portable device 122 to be directly exposed to incident UV radiation from the UV lamps 118 without the need for mirrors/reflectors to direct the UV radiation onto external surfaces of the portable device 122 that are not in the direct path of incident UV radiation.

This arrangement has several advantages compared to existing sanitation systems. First, it allows for uniform sanitation of all the surfaces of the portable device 112 without having to manipulate the portable device 112 inside the sanitizer 100 to ensure all sides have been exposed to sufficient UV radiation. The benefit is that the portable device 112 is less likely to be scratched or damaged since no manipulation of the device is required. A further advantage is that the time required for sanitation is shortened. For example, a sanitation time as short as 20 seconds may be sufficient where all surfaces of the portable device 122 are exposed to direct UV-C radiation dose of at least 12 mJ/cm$^2$.

Referring back to FIG. 1A, when the doors 106 are in the closed position (as shown), no UV radiation can escape the sanitizer 100 through the opening 102 while the sanitizer 100 is in operation. This is beneficial to protect the eyesight of users compared to existing UV sanitation systems that are not fully enclosed and have the potential to leak harmful UV radiation that is damaging to eyesight.

Figure 2:
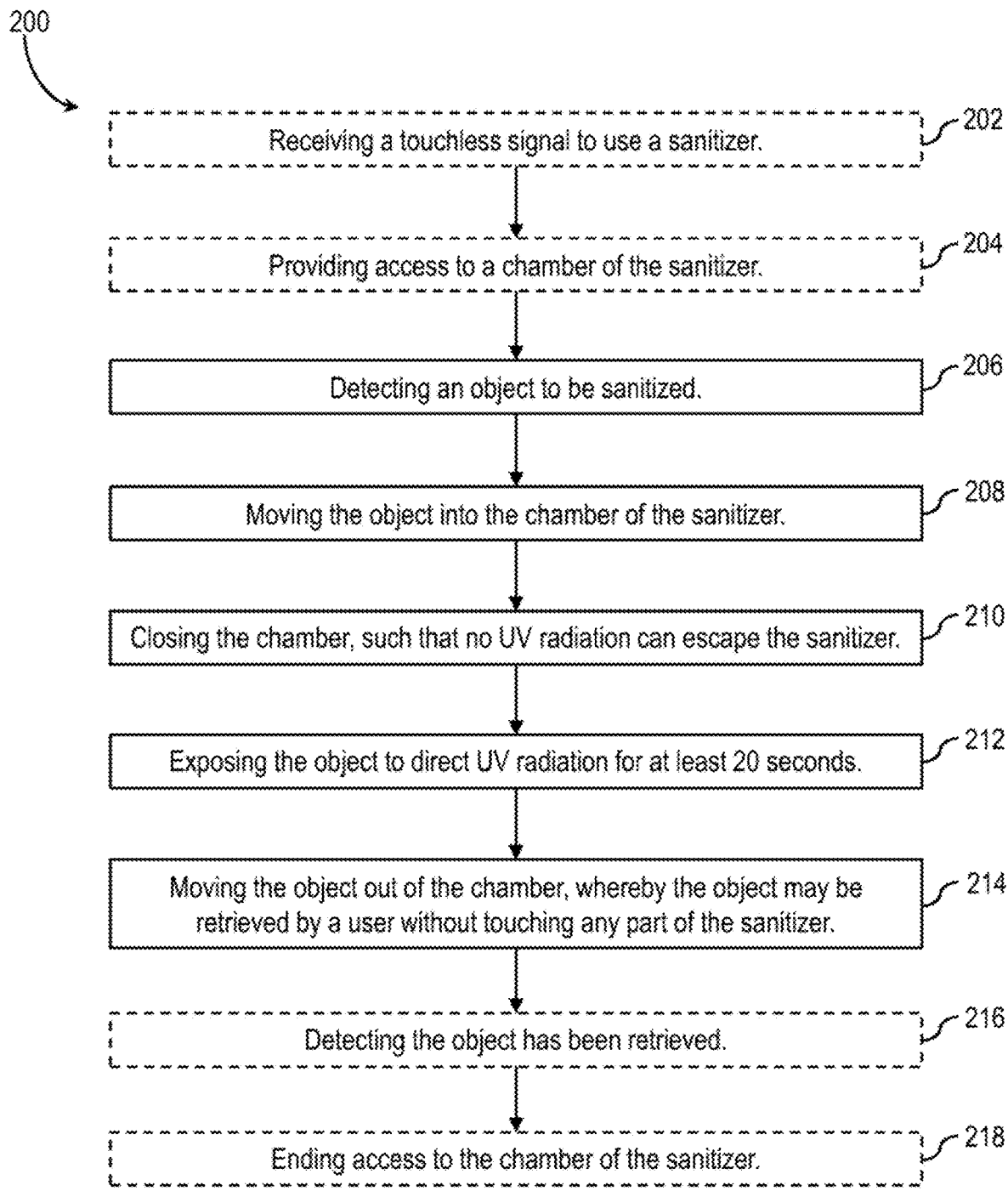
FIG. 2 is a flow chart of a method for touchless sanitation of objects, in accordance with an embodiment.

Referring to FIG. 2, illustrated therein is a flow chart of a method 200 for touchless sanitation of objects, according to an embodiment. The method 200 may be used for quick and efficient disinfection or sanitation of portable electronic devices and other handheld objects, such as keys or a wallet. The method 200 may be implemented using the sanitizer 100 shown in FIGS. 1A-1H, sanitizer 300 in FIGS. 3A-3C or sanitizer 400 in FIGS. 4A-4D. In the description of method 200, the elements from FIG. 1E are indicated in parenthesis for reference.

At 202, a touchless signal to use a sanitizer (100) is received. The touchless signal is received by a detector (108) on the sanitizer (100). The signal may be received when a user triggers the detector (108) by holding their hand or the object (122) to be sanitized in close proximity to the detector (108). The touchless signal may be an infrared (IR) signal sent by a portable device (122), a thermal infrared signal from the user's body heat, a load sensor that recognizes the weight of a portable device (122), an RFID signal or an NFC signal sent by a portable device (122). The touchless signal may be NFC signal for secure payment.

At 204, access to the chamber (112) of the sanitizer (100) is provided. Access is provided by opening the doors (106) and raising the platform (116) so that the object (122) to be sanitized may be placed on the platform (116) by the user. The opening of the doors (106) and raising of the platform (116) are mechanically coupled and controlled by an actuator (120).

According to some embodiments, acts 202 and 204 may be omitted and the method 200 commences at Act 206. For example, where payment is not required to use the sanitizer (100), the doors (106) may be open, by default, for a user to place an object (122) into the platform (116) and commence sanitation.

At 206, the object (122) to be sanitized is detected. The object (122) is detected by a load sensor in the platform (116). For example, an increase in the force measured by the load sensor may indicate that the object (122) has been placed on the platform (116) by the user.

At 208, the object (122) is moved into the chamber (112) of the sanitizer (100). The object (122) is moved by lowering the platform (116) to its lowest position so that the object (122) is wholly within the chamber (112).

At 210, the chamber (112) is closed such that no UV radiation can escape the sanitizer (100). The chamber (112) is closed by closing the doors (106), effectively sealing the sanitizer (100) and preventing UV radiation from escaping the sanitizer (100). According to some embodiments, the sanitizer (100) includes a thermal infrared detector adjacent to the door (106) for detecting whether a user's hand is blocking the door (106) from closing. Acts 208 and 210 may be performed concurrently.

At 212, the object (122) is sanitized by exposure to direct UV radiation for at least 20 seconds. The UV radiation is emitted by a plurality of UV radiation sources (118) within the sanitizer (100). The radiation sources (118) are positioned around the chamber (112), such that all surfaces of the object (122) are directly exposed to incident UV radiation.

At 214, the object (122) is moved out of the chamber (112) whereby the object may be retrieved by the user without touching any part of the sanitizer (100). The object (122) is moved out by opening the doors (106) and raising the platform (116) to its highest position, so that at least a portion of the object (122) protrudes out of the chamber (112) and outside sanitizer (100). The object may protrude above or out of the sanitizer 100, depending on the embodiment (side slot entry type of device may eject out and not up). The object (122) may then be retrieved by the user without touching any part of the sanitizer (100). The opening of the doors (106) and raising of the platform (116) are mechanically coupled and controlled by the actuator (120).

At 216, retrieval of the sanitized object (122) by the user is detected. Retrieval of the object (122) is detected by the load sensor in the platform (116). For example, a decrease in the force measured by the load sensor may indicate that the object (122) has been retrieved by the user.

At 218, access to the chamber (112) is ended by lowering the platform (116) closing the doors (106) of the sanitizer (100). The closing of the doors (106) and lowering of the platform (116) are mechanically coupled and controlled by the actuator (120). According to some embodiments, wherein the method 200 commences at Act 206, Acts 216 and 218 may be omitted, and the method 200 concludes at Act 214.

The sanitizer (100) is configured to automatically perform Acts 202 to 218. Thus, the method 200 may be performed without needing a user to make any physical contact with the sanitizer (100). However, a user must take care not to make physical contact with the sanitizer (100) between Acts 204 and 206, when placing the object (122) to be sanitized on the platform (116), and between Acts 214 and 216 when retrieving the sanitized object (122).

According to an embodiment, the sanitizer 100 may be configured to perform "self-cleaning" whereby the interior of the sanitizer 100, including the chamber 112 and underside of the doors 106 is sanitized. For example, self-cleaning may comprise the performance of Acts 210 and 212 from the method 200, absent an object 122 in the chamber 112. According to an embodiment, the method 200 may be implemented in one or more operational modes in a sanitizer (see FIG. 5A).

Figure 4A:
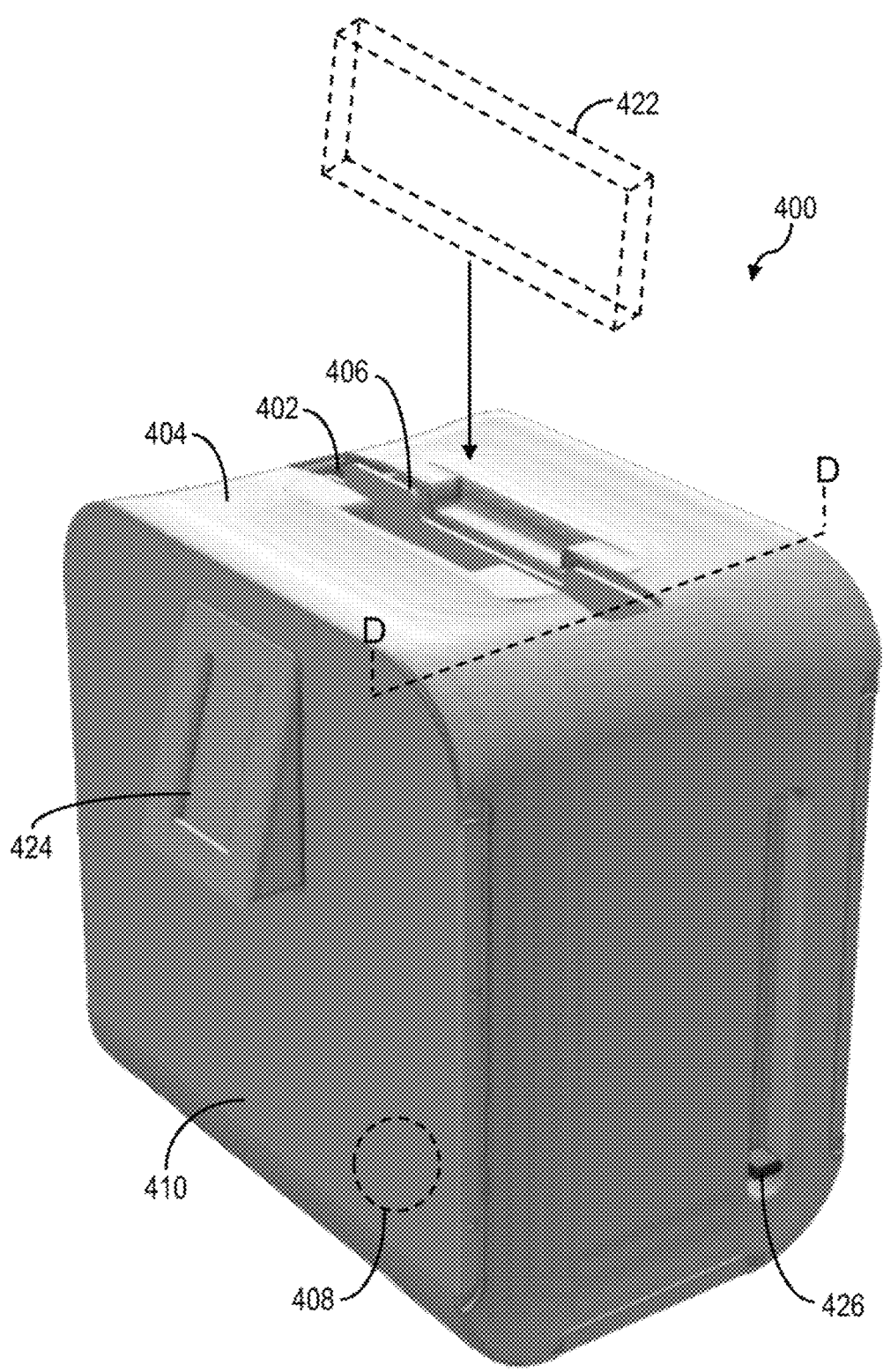
FIG. 4A is a perspective view of a sanitizer shown in relation to a mobile device, in accordance with an embodiment.
Figure 4B:
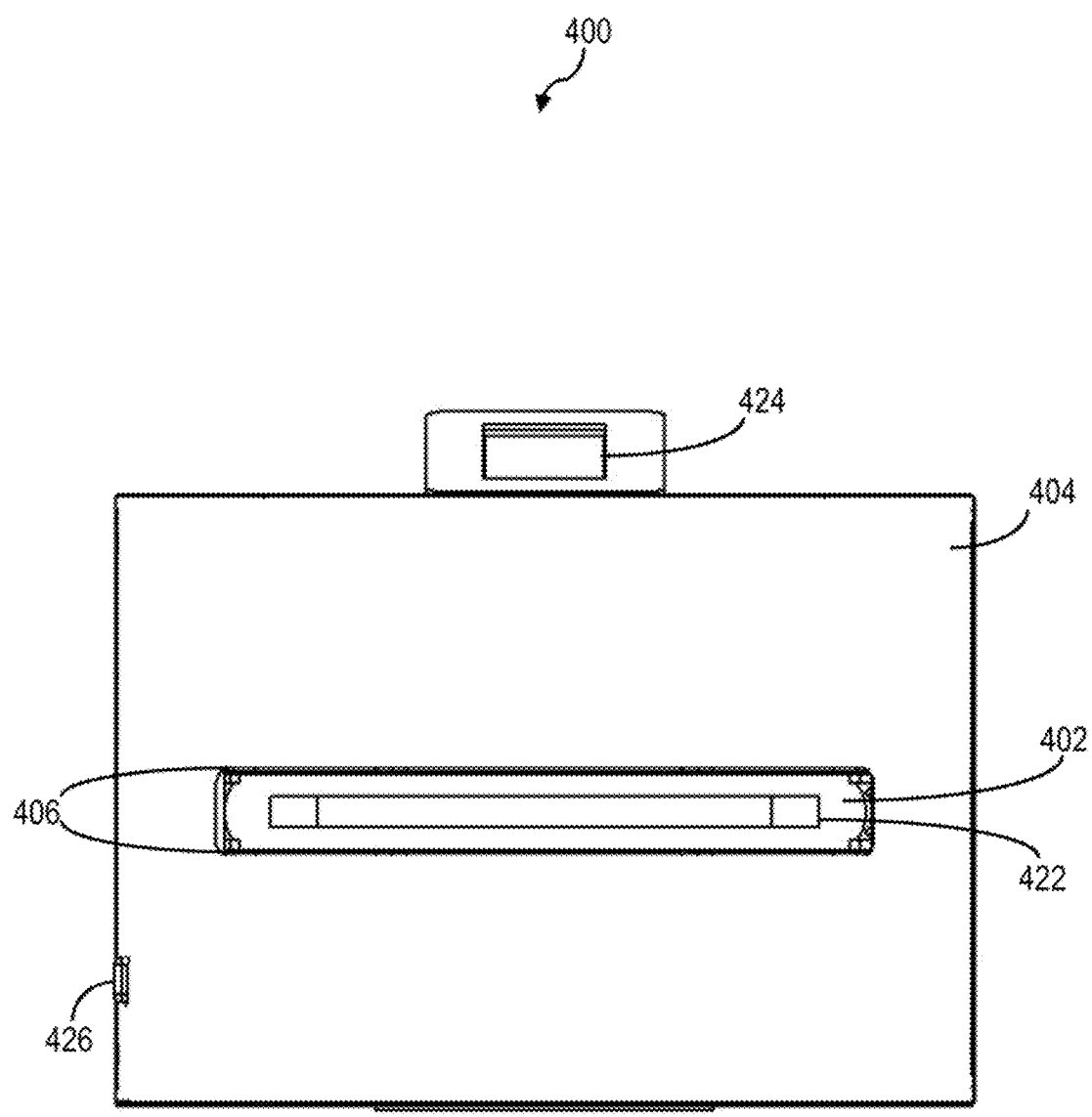
FIG. 4B is a top view of the sanitizer in FIG. 4A, shown in relation to a mobile device.
Figure 4C:
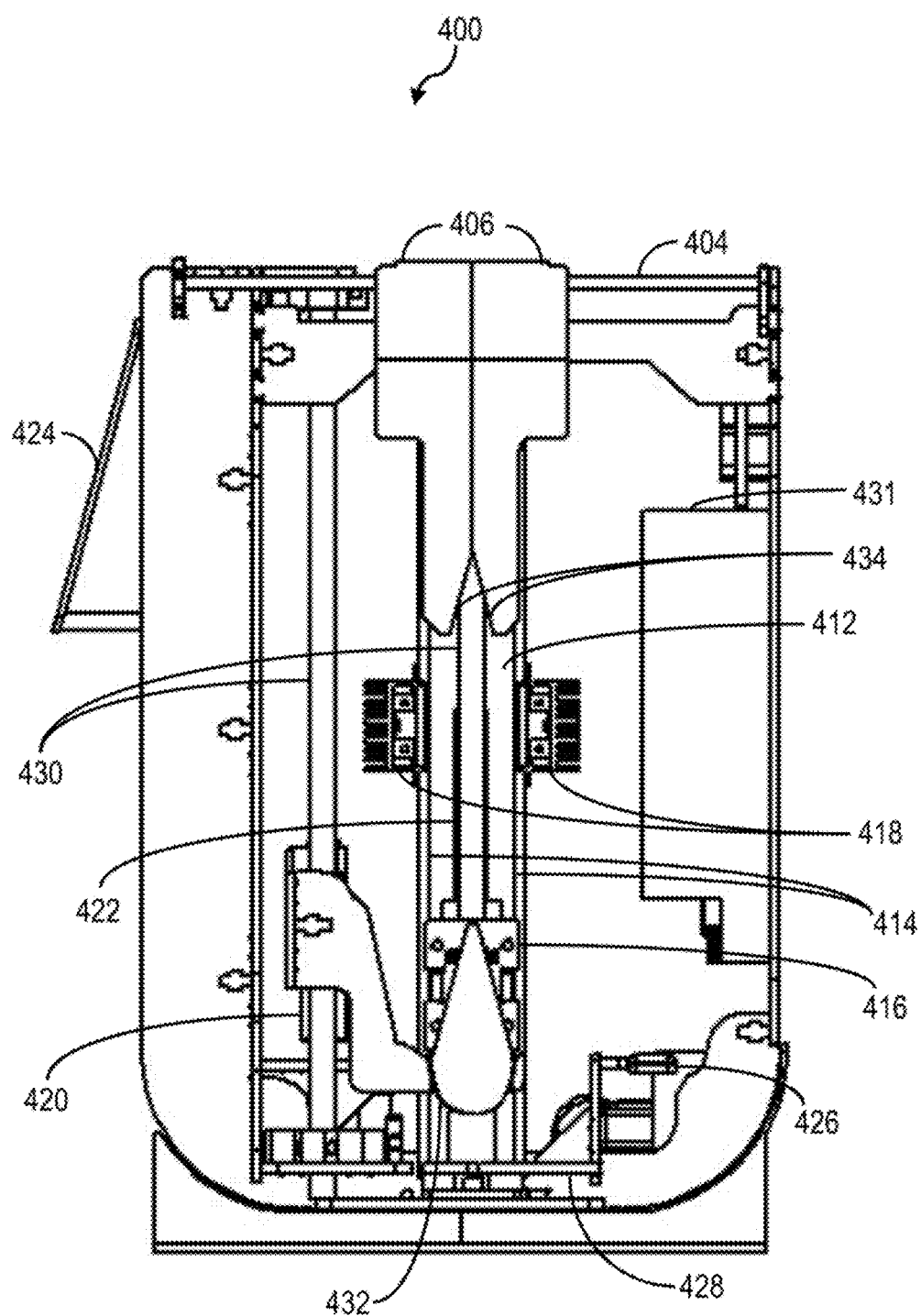
FIG. 4C is a side cross-sectional view through section D-D of the sanitizer in FIG. 4A, during sanitation.
Figure 4D:
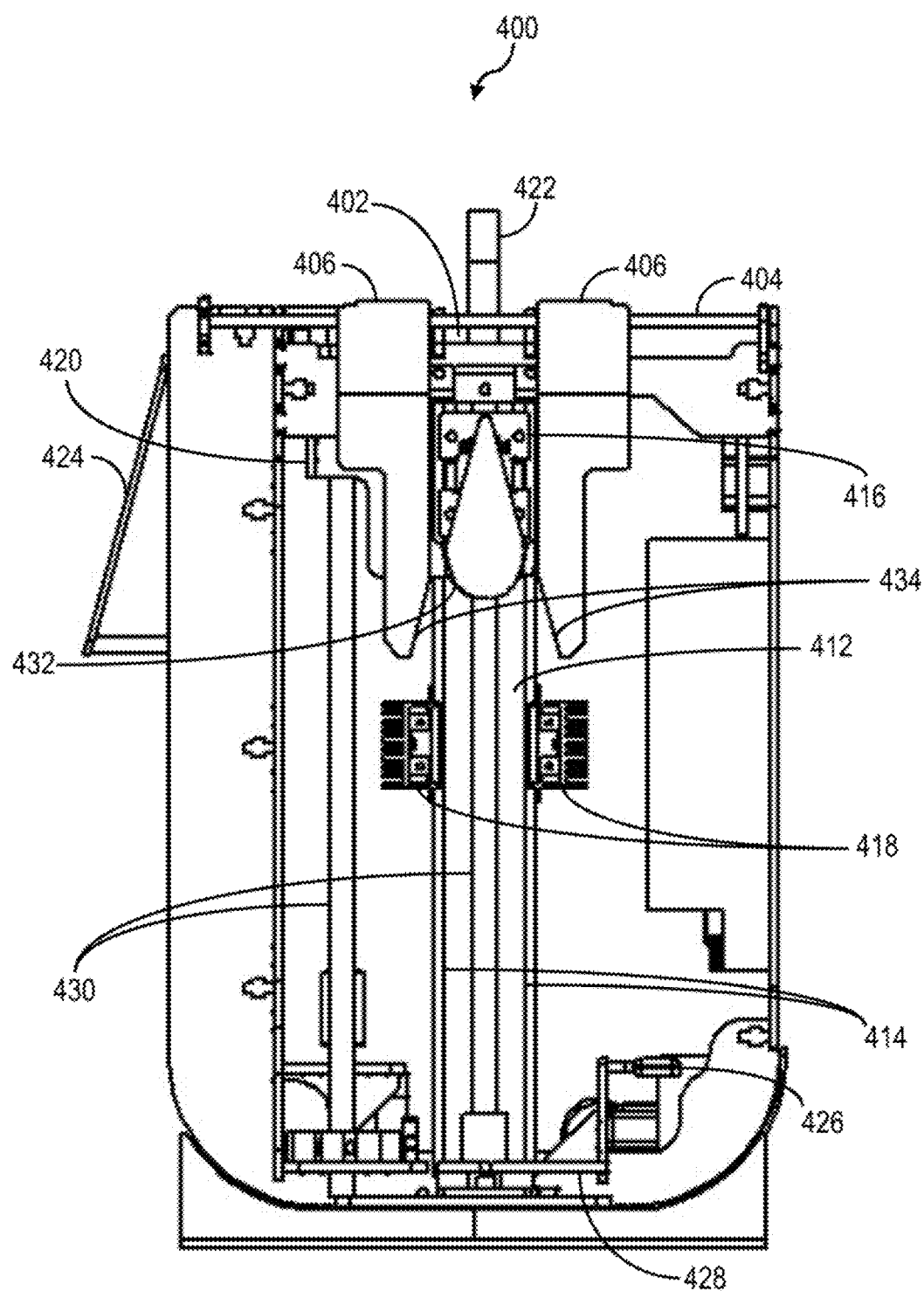
FIG. 4D is a side cross-sectional view through section D-D of the sanitizer in FIG. 4A, during entry and exit of a mobile device.

Referring to FIG. 4A, illustrated therein is a sanitizer 400, according to an embodiment. The sanitizer 400 includes an opening 402 in a top surface 404 of the sanitizer 400. The opening 402 is large enough for a mobile device 422 (i.e. a smartphone or tablet) to pass through the opening 402 into the sanitizer 400. The opening 402 is covered by at least one moveable door 406 (shown in an open position). Preferably, the sanitizer 400 includes two moveable doors 406 as shown in FIGS. 4B-4D.

The sanitizer 400 includes a detector 408 in an external surface 410 of the sanitizer 400 for detecting a magnetic key fob (not shown). The detector 408 may be a radio-frequency identification (RFID) receiver, magnetic, or other near-field communication (NFC) receiver. The magnetic key fob may be used to activate or switch an operational mode of the sanitizer 400 (see FIG. 5A).

The sanitizer 400 includes a display screen for displaying instructions and/or the operational status of the sanitizer 400. For example, during sanitation the display screen 424 may display a countdown timer indicating the amount of time until sanitation is complete. The display screen 424 may also display error messages/codes when an error is encountered during operation of the sanitizer 400. The display screen 424 may also display advertisements or other information. As shown, the detector 308 and display screen 424 are positioned on the same external surface 410 of the sanitizer 400. According to other embodiments, the detector 408 and screen 424 may be on different surfaces of the sanitizer 400.

The sanitizer 400 includes an emergency recovery handle 426. The recovery handle 426 may be manually raised by a user to eject the mobile device 422 from the sanitizer 400 if power is lost or if the sanitizer 400 encounters an error during sanitation and cannot eject the mobile device 422 normally.

The relatively small form factor of the sanitizer 400 allows the sanitizer 400 to be installed and used in an unobtrusive manner in a variety of locations throughout a workplace. The sanitizer 400 may be placed on a table, countertop or stand. The sanitizer 400 may be mounted to a wall. The sanitizer 400 may be located on the exterior of a building and constructed with appropriate weather-proofed materials.

Referring to FIGS. 4C and 4D, illustrated therein are side cross-sectional views of the sanitizer 400 through section D-D in FIG. 4A. FIG. 4C shows the sanitizer 400 during sanitation, wherein the mobile device 422 is wholly within the sanitizer 400. FIG. 4D shows the sanitizer 400 during entry or exit of the mobile device 422.

The sanitizer 400 includes a chamber 412 for receiving the mobile device 422. The chamber 412 is bounded by opposable reflective walls 414, a moveable platform 416 and the doors 406. The mobile device 422 is placed on the platform 416 and moved into the sanitizer 400 for sanitation. According to an embodiment, the moveable platform 416 may include a conveyor or a holster shaped to grip the mobile device 422. The moveable platform 416 may include a load sensor/switch (not shown) to detect when the mobile device 422 is on the platform 416.

The sanitizer 400 includes an actuator 420 connected to the platform 416 for vertically moving the platform 416 between the reflective walls 414. The actuator 420 moves vertically along one or more support columns 430. The actuator 420 may be an electromechanical actuator 420, for example, a rack and pinion operatively connected to a motor, for raising and lowering the platform 416. The actuator 420 may be a linear motor-screw actuator. The actuator 420 may be a belt-driven actuator.

According to an embodiment, the actuator 420 may further be operatively connected to the doors 406, to control opening and closing of the doors 406. The movement of the platform 416 by the actuator 420 may be mechanically coupled to the opening/closing of the doors 406. For example, the actuator 420 moving the platform 416 downward may cause the doors 406 to close once the platform 416 reaches a predetermined position during downward travel. Conversely, the actuator 420 moving the platform 416 upward may cause the doors 106 to open once the platform 416 reaches a predetermined position during upward travel.

The platform 416 includes a wedge member 432. The wedge member 432 contacts angled surfaces 434 on the underside of the doors 406 as the platform 416 is raised by the actuator 420. The doors 406 are biased to the closed position and the upward force exerted by the wedge member 432 on the angled surfaces 434 cause the doors 406 to open (FIG. 4D). Conversely, when the platform 416 is lowered by the actuator 420, the wedge member 432 disengages from the angled surfaces 434 and the doors 406 close (FIG. 4C).

The platform 416 may also be raised manually to eject the mobile device 422 by lifting the recovery handle 426. As noted above, manual ejection may be required if power is lost or if the sanitizer 400 encounters an error during operation. The recovery handle 426 is connected to the platform 416 by a support arm 428. Lifting the recovery handle 426 causes the support arm 428 to contact a bottom of the platform 416 and raise the platform 416 and wedge member 432 upward. As the recovery handle 426 (and platform 416) is raised, the wedge member 432 contacts the angled surfaces 434 of the doors 406 and forces the doors 406 to open.

The sanitizer 400 includes a pair of UV-C LED printed circuit boards 418 for emitting high intensity UV-C radiation into the chamber 412. The LED printed circuit boards 418 are opposed positioned either side of the chamber 412 at approximately the midpoint height of the sanitizer 400. This arrangement allows for the mobile device 422 on the platform 416 to be lowered and raised between the LED printed circuit boards 418 during sanitation to ensure all external surfaces of the mobile device 422 are exposed to an appropriate dosage of UV-C radiation. According to an embodiment, the sanitizer 400 may include the LED printed circuit boards 418 positioned adjacent to the doors 406 thereby allowing for a shorter height of the sanitizer 400.

The height of the chamber 412 is sufficient to allow a mobile device 422 to pass by the LED printed circuit boards 418 on downward travel and again on upward travel, all while the doors 406 are closed to prevent the escape of UV-C radiation from the chamber 412. The mobile device 422 is preferably inserted into the sanitizer 400 with the longitudinal axis of the mobile device 422 aligned with the longitudinal axis of the opening 402 (FIGS. 4A-4B). Thus, the height of the chamber 412 is preferably at least two times the width of the mobile device 422.

The width of the chamber 412 is preferably no more than double the thickness of the mobile device 422 so that the LED printed circuit boards 418 are positioned as close as possible to the surfaces of the mobile device 422 to maximize the dosage of UV-C light that is incident on the mobile device 422 and to minimize sanitation time. Preferably, the distance between the LED printed circuit boards 418 and the external surface of the mobile device 422 is no more than 2 cm when the mobile device 422 passes between the LED printed circuit boards 418.

The opposable reflective walls 414 concentrate the UV-C radiation to the chamber 412 to shorten sanitation time and ensure all external surfaces of the mobile device 422 are sanitized. The opposable reflective walls 414 and the underside of the doors 406 facing the chamber 412 may be coated with reflective paint, or may be constructed of reflective materials, preferably aluminum or Teflon™ to achieve at least 25% reflectivity.

Figure 4E:
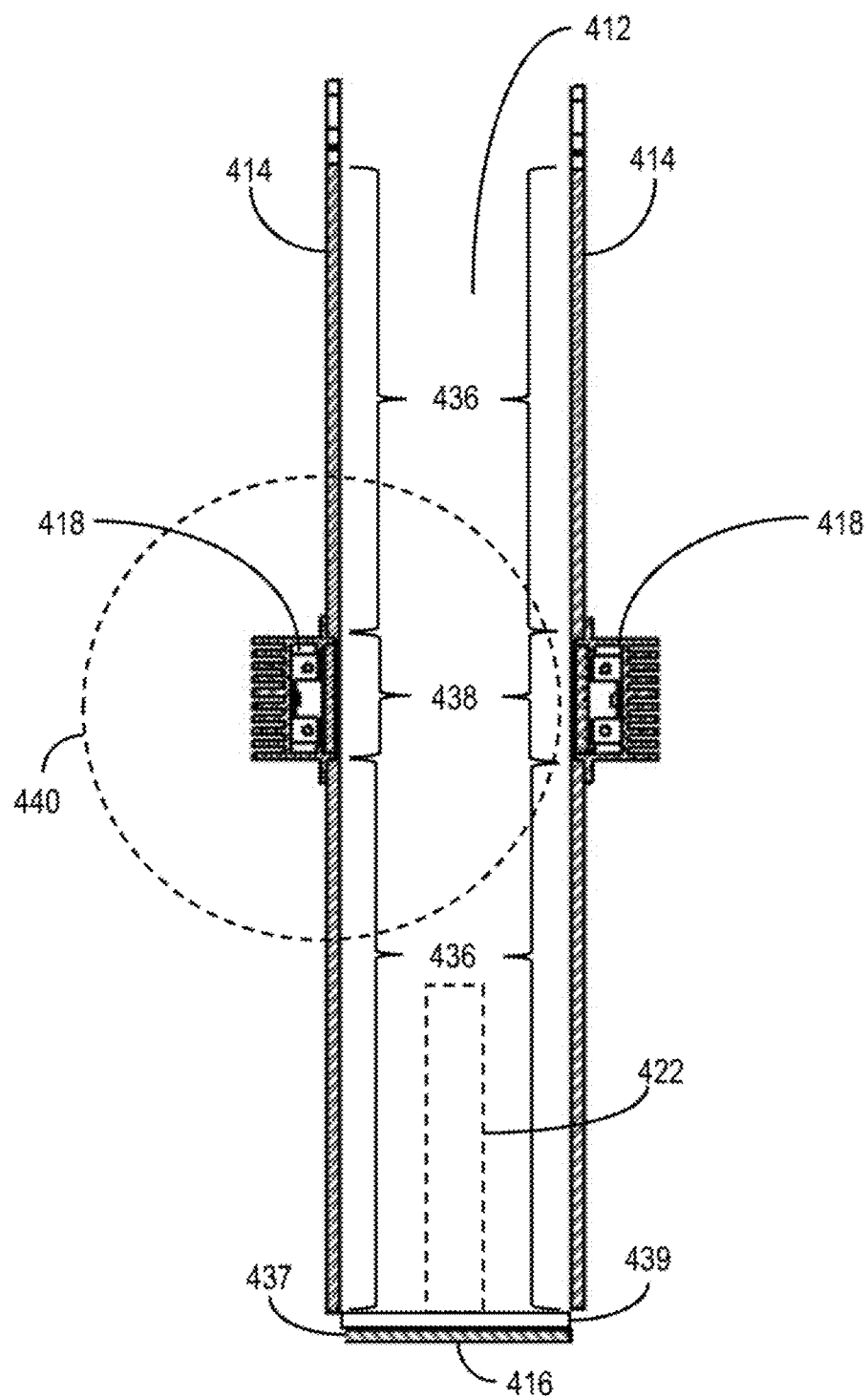
FIG. 4E is a magnified view of the chamber in FIGS. 4C-4D.

Referring to FIG. 4E, illustrated therein is a magnified view of the chamber 412. For ease of illustration, the mobile device 422 is not shown to scale. The reflective wall 414 includes reflective regions 436 adjacent to the LED printed circuit boards 418 to reflect the UV-C radiation emitted by the LED printed circuit boards 418. Similarly, a top surface 437 of the platform 416 includes reflective paint, or Teflon to ensure the surface of the mobile device 422 that contacts the platform 416 is sanitized, with at least reflected UV-C radiation, if not by direct incident UV-C radiation as the platform 416 is lowered and raised during sanitation.

Quartz glass 438 covers the LED printed circuit boards 418 as a window to allow UV-C radiation projected by the LED printed circuit boards 418 to pass into the chamber 412.

Quartz glass 439 also covers the reflective top surface 437 of the platform 416 to raise the mobile device 422 above the reflective top surface 437 of the platform 416 so that the surface of the mobile device 422 in contact with the platform 416 is sanitized by UV-C radiation reflected off the reflective top surface 437.

Quartz glass 438, 439 is preferred for this application for its high optical transmittance (at least 88%) of UV-C radiation. The quartz glass 438 further protects the LED printed circuit boards 418 and forms a smooth interface with the reflective wall 414 to ensure no part of the mobile device 422 gets caught against the reflective wall 414 when the platform 416 is raised or lowered.

Figure 4F:
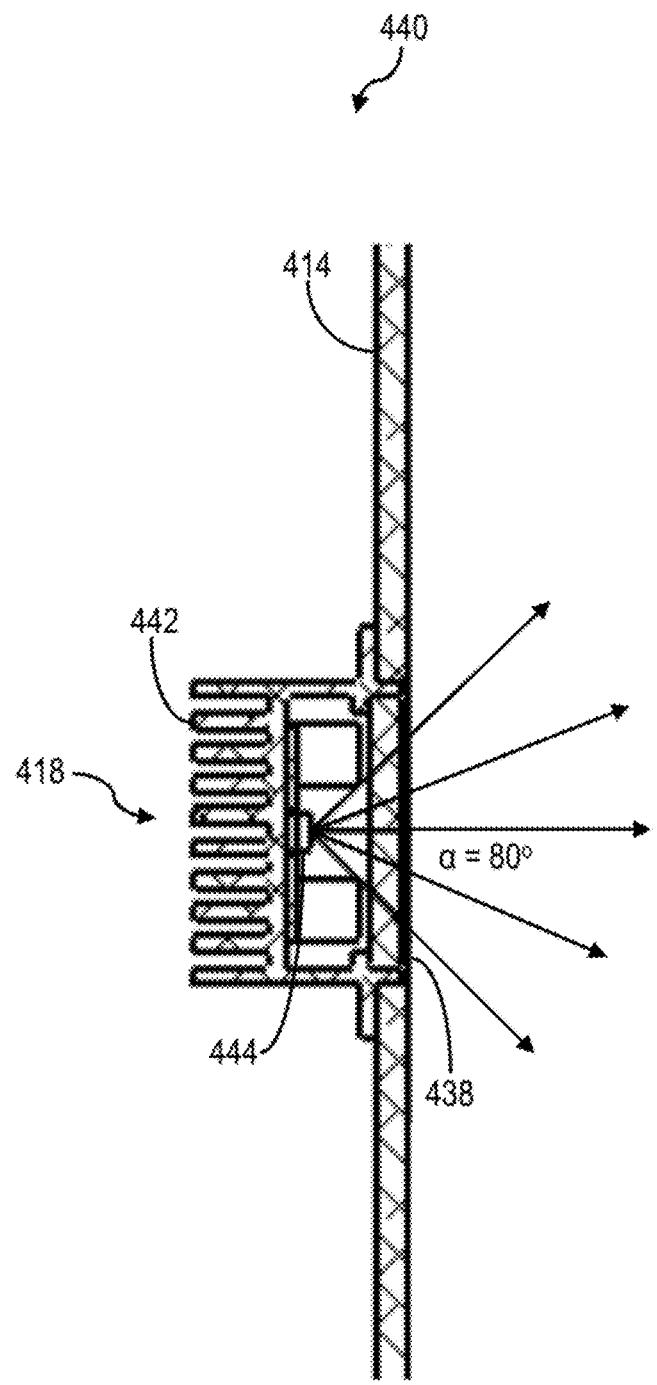
FIG. 4F is a magnified view of the LED printed circuit board in FIG. 4E.

Referring to FIG. 4F, illustrated therein is the region 440 in FIG. 4E, showing a magnified view of the LED printed circuit board 418. The LED printed circuit board 418 includes an LED bar 444 having a plurality of UV-C LEDs. The LED bar 444 is covered by the quartz glass 438. The LED printed circuit board 418 includes a heat sink 442 for dissipating heat from the LED bar 444. According to another embodiment, the LED printed circuit board 418 may include one or more fans for cooling.

Figure 4G:
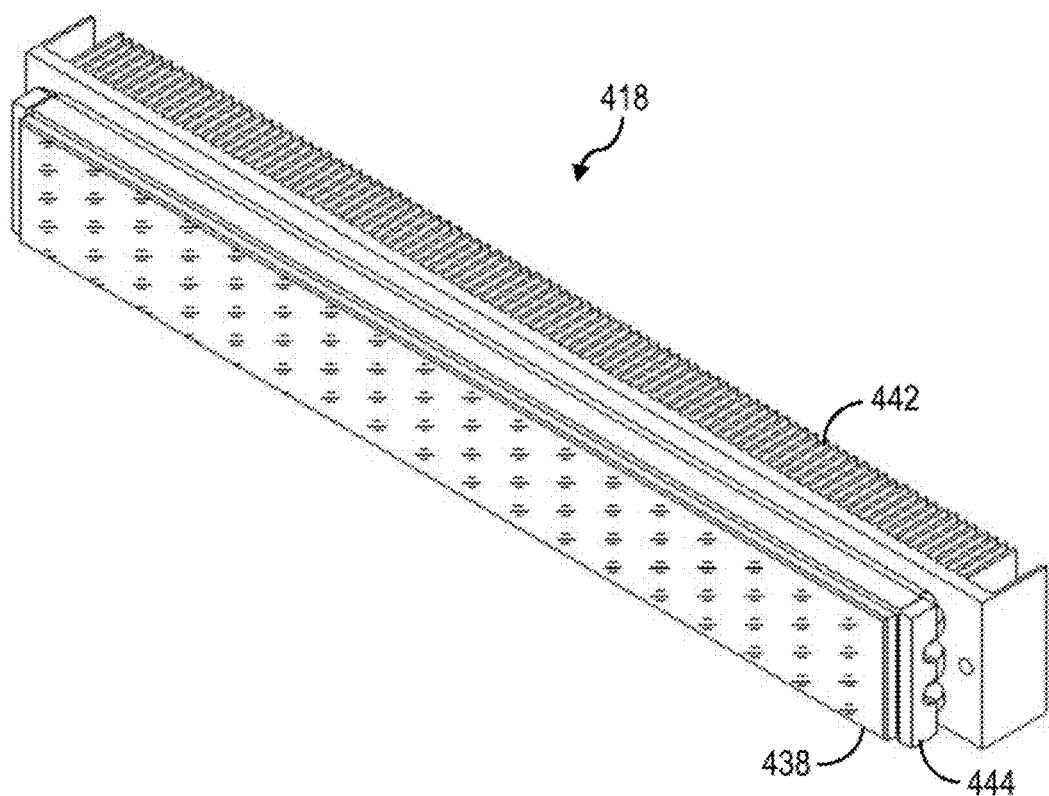
FIG. 4G is a perspective view of the LED printed circuit board, in accordance with an embodiment.

Referring to FIG. 4G illustrated therein is a perspective view of the LED printed circuit board 418 showing the LED bar 444, quartz glass 438 and heat sink 442.

Figure 4H:
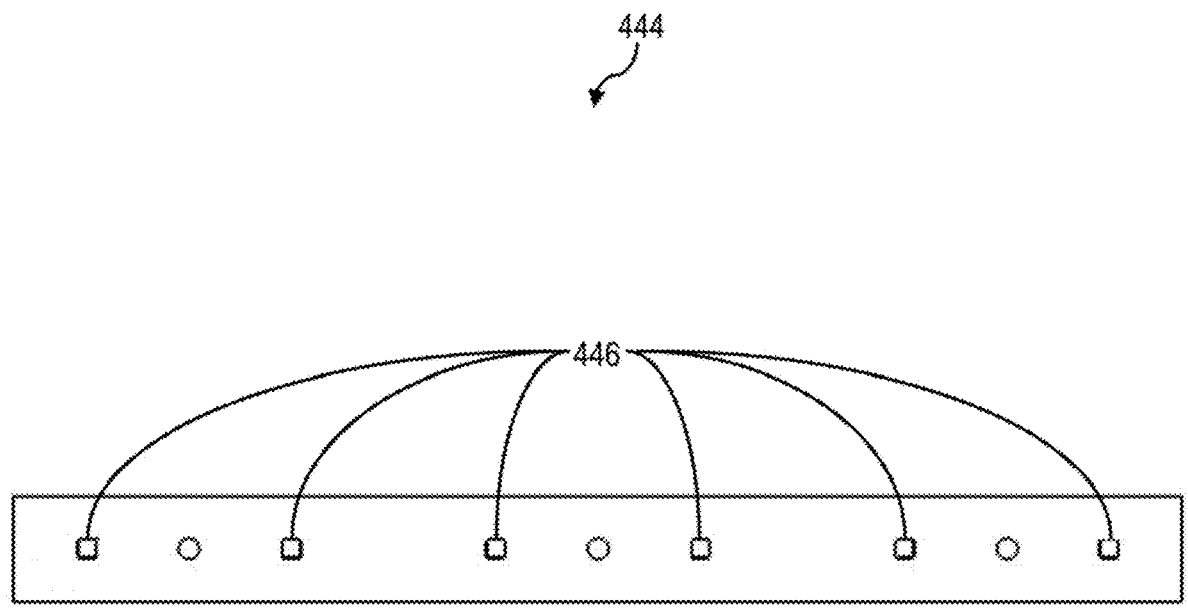
FIG. 4H is a front view of the LED bar in FIG. 4G, as seen through the quartz glass.

Referring to FIG. 4H, illustrated therein is a front view of the LED bar 444 in FIG. 4G, as seen through the quartz glass 438. The LED bar 444 includes a plurality of UV-C LEDs 446 spaced at intervals to ensure relatively uniform UV-C radiation exposure to all parts of the mobile device. Each UV-C LED 446 is capable of at least 50 mW output.

Referring again to FIG. 4F, the LED printed circuit board 418 generates approximately 2.5-6.3 $mJ/cm^2$ of UV-C radiation per second. The range assumes the LED bar 444 produces ~130 degrees of exposure through the quartz glass 438 and the surface of the mobile device 422 will be at an angle relative to the radiation emitted from the LED bar 444 thus exposure is not constant across the surface of the mobile device. Given this per second dosage and assuming a worst-case scenario (i.e. 2.5 $mJ/cm^2$ per second), each surface of the mobile device must be exposed to the UV-C radiation for ~5 seconds to achieve a cumulative dosage of at least 12 $mJ/cm^2$. It has been shown that the cumulative UV-C (275 nm) dosage required to kill 99.99% of Methicillin-resistance *Staphylococcus aureus* (MRSA) bacteria, typically used as a standard in the testing of sanitizing devices, is 12 $mJ/cm^2$.

According to an embodiment, the LED printed circuit board 418 may include a UV-C sensor to measure the emitted UV-C radiation to ensure the LEDs are properly functioning and the dosage of UV-C radiation is sufficient. If the dosage is deemed to be insufficient, an error code may be displayed on the screen of the sanitizer.

Referring again to FIG. 4C, the sanitizer 400 includes a control unit 431. The control unit 431 houses electrical components for connecting the sanitizer 400 to an AC power source (e.g. a power socket). The control unit 431 includes a current balancing circuit. Due to high power consumption by the LED printed circuit boards 418 the current balancing circuit includes a constant current driver to convert the AC current to DC current that is supplied in parallel to the LED printed circuit boards 418.

The control unit 431 includes a safety relay prior to the power source to cut power to the LED printed circuit boards 418 in the event the doors 406 are forced open (i.e. by raising the recovery handle 426 while the sanitizer 400 is operating normally) to ensure no UV-C radiation escapes the chamber 412. Thus, the safety relay ensures that the LEDs may only be switched on when the doors 406 are closed. A further security feature is that power is cut in the event the external case of the sanitizer is opened.

The control unit 431 includes a control circuit, including a computer processor operably coupled to a memory for storing processor-executable instructions. When executed by the processor, the instructions govern the automated, touchless operation of the sanitizer 400 without the need for the user to input settings. This is advantageous in preventing potential cross-contamination caused by users touching the sanitizer 400. The instructions governing operation of the sanitizer 400 may be programmed as a series of operations modes as described below.

Figure 5A:
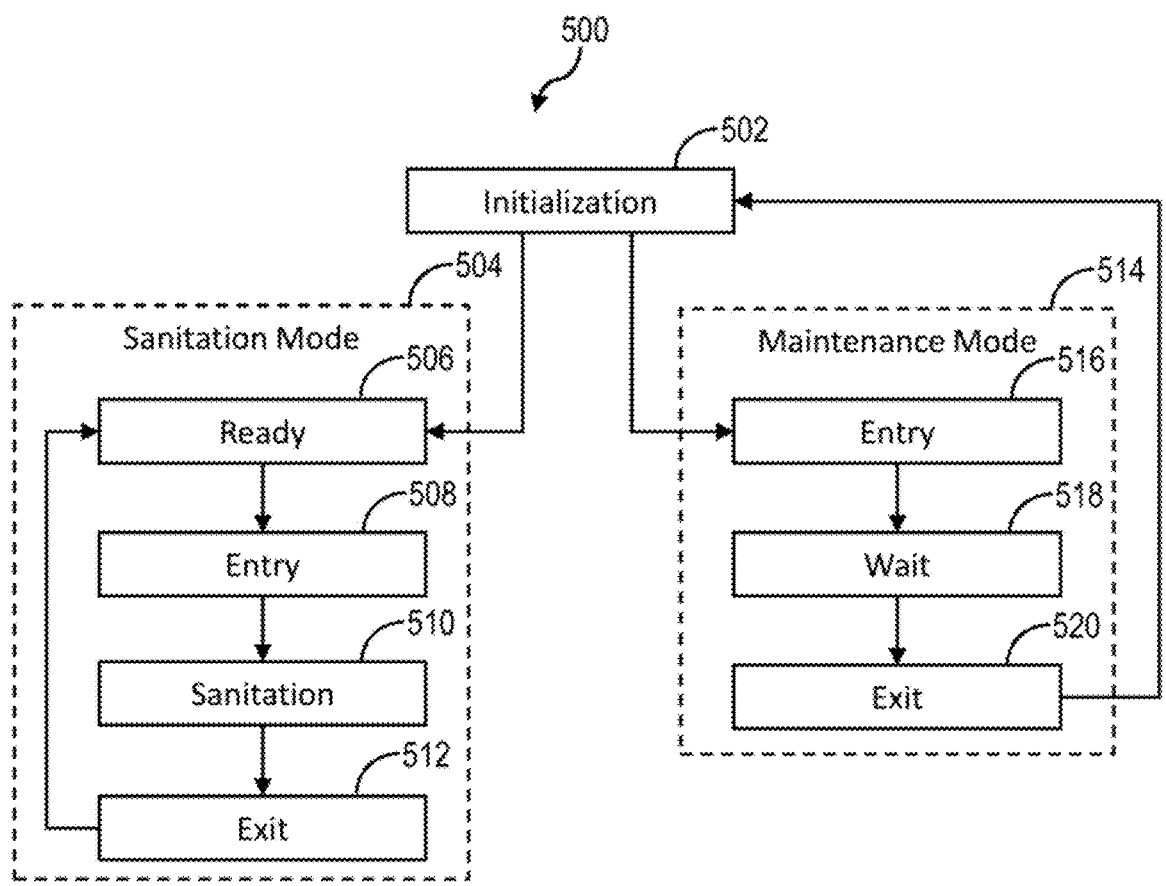
FIG. 5A is a flow chart of operational modes for a sanitizer, in accordance with several embodiments.

Referring to FIG. 5A, illustrated therein is a flow chart of operational modes 500 for a sanitizer, according to several embodiments. The operational modes 500 may be executed by the sanitizer 100 in FIGS. 1A-1H, sanitizer 300 in FIGS. 3A-3C or sanitizer 400 in FIGS. 4A-4D.

At 502, upon being powered on, the sanitizer performs an initialization sequence (FIGS. 5B-5C) to ensure key components are operating correctly.

Following the initialization sequence 502, the sanitizer may enter a sanitation mode 504 or a maintenance mode 514. Sanitation mode 504 is executed for sanitizing objects; maintenance mode 514 is executed for cleaning and sanitation of the sanitizer itself. The sanitizer may be configured to enter sanitation mode 504 by default, upon completion of the initialization sequence 502.

If the sanitation mode 504 is executed, the sanitizer enters a ready state 506. During the ready state, the screen of the sanitizer may display a message, for example, "ready to sanitize, please insert phone to begin." The sanitizer remains in the ready state until a user places a mobile device to be sanitized onto the platform.

Figure 5B:
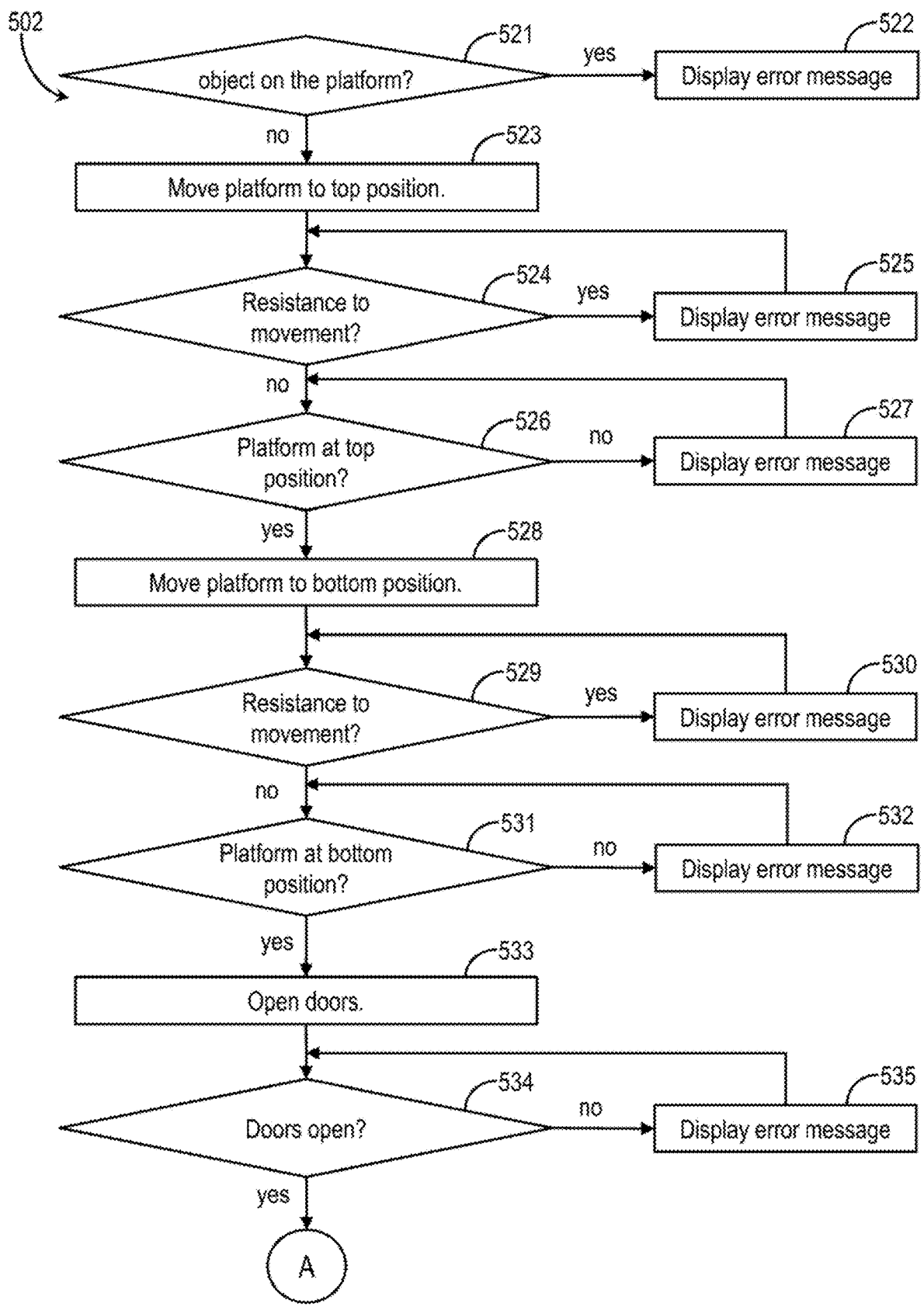
FIGS. 5B-5C is a flow chart of an initialization sequence, in accordance with an embodiment.
Figure 5C:
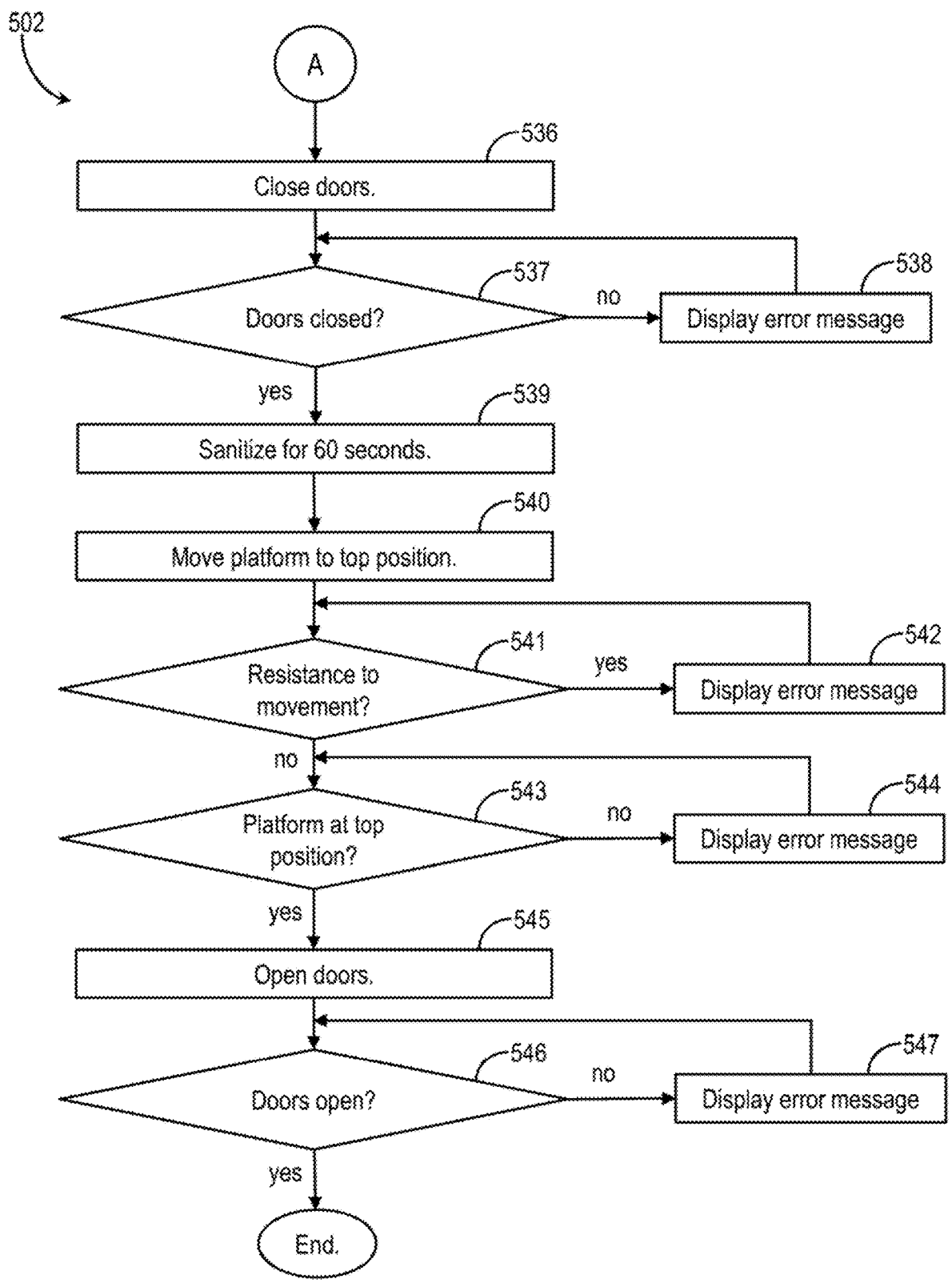
Figure 5D:
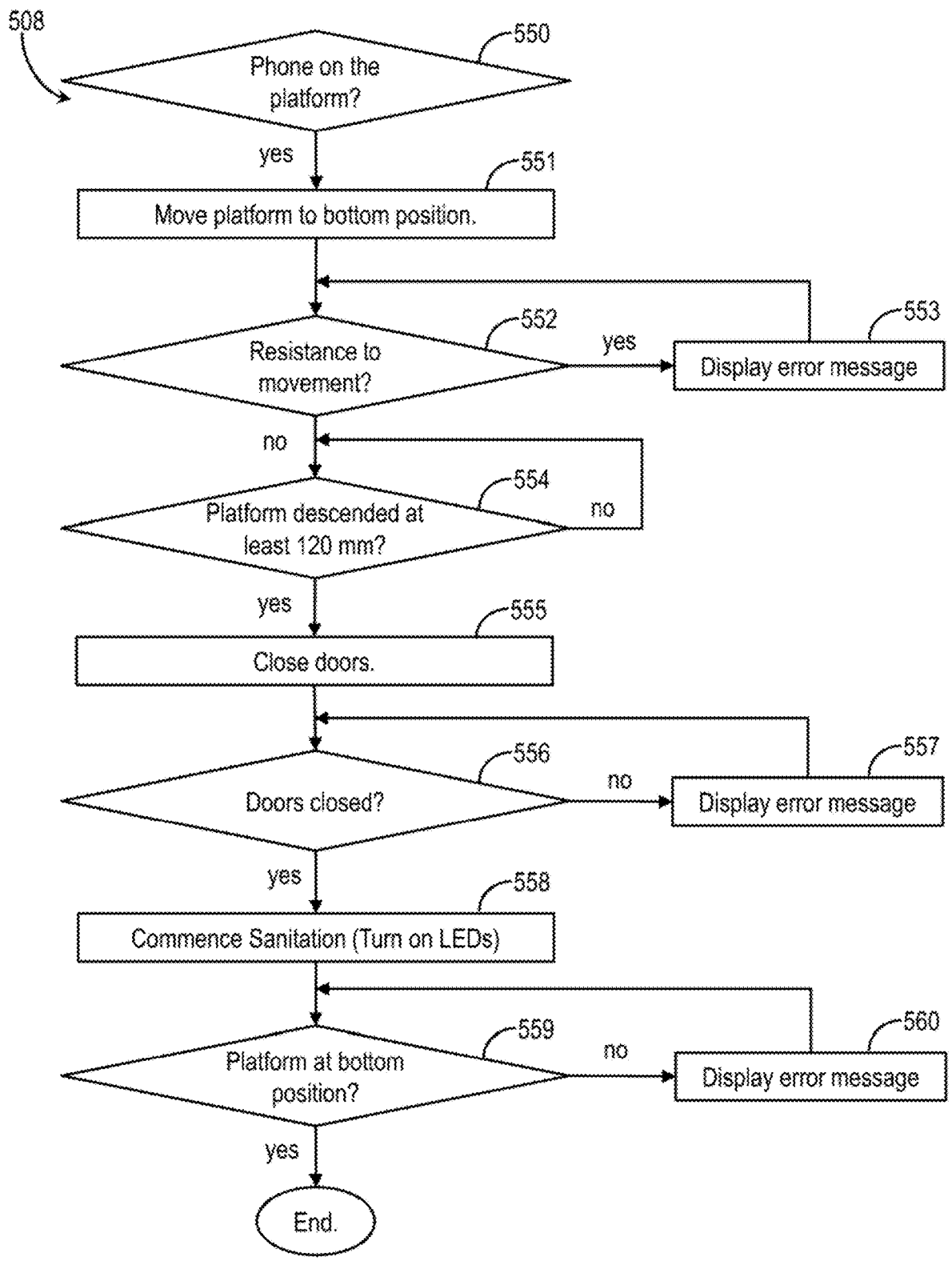
FIG. 5D is a flow chart of an entry state, in accordance with an embodiment.

Upon detection of the mobile device on the platform (by the load sensor in the platform), the sanitizer enters an entry state 508 (FIG. 5D). During the entry state 508, the phone is lowered into the sanitizer on the platform, the doors are closed, the UV-C LEDs are switched on and sanitation commences. During the entry state, the screen of the sanitizer may display a message, for example, "Beginning sanitation. Please wash or sanitize your hands."

Figure 5E:
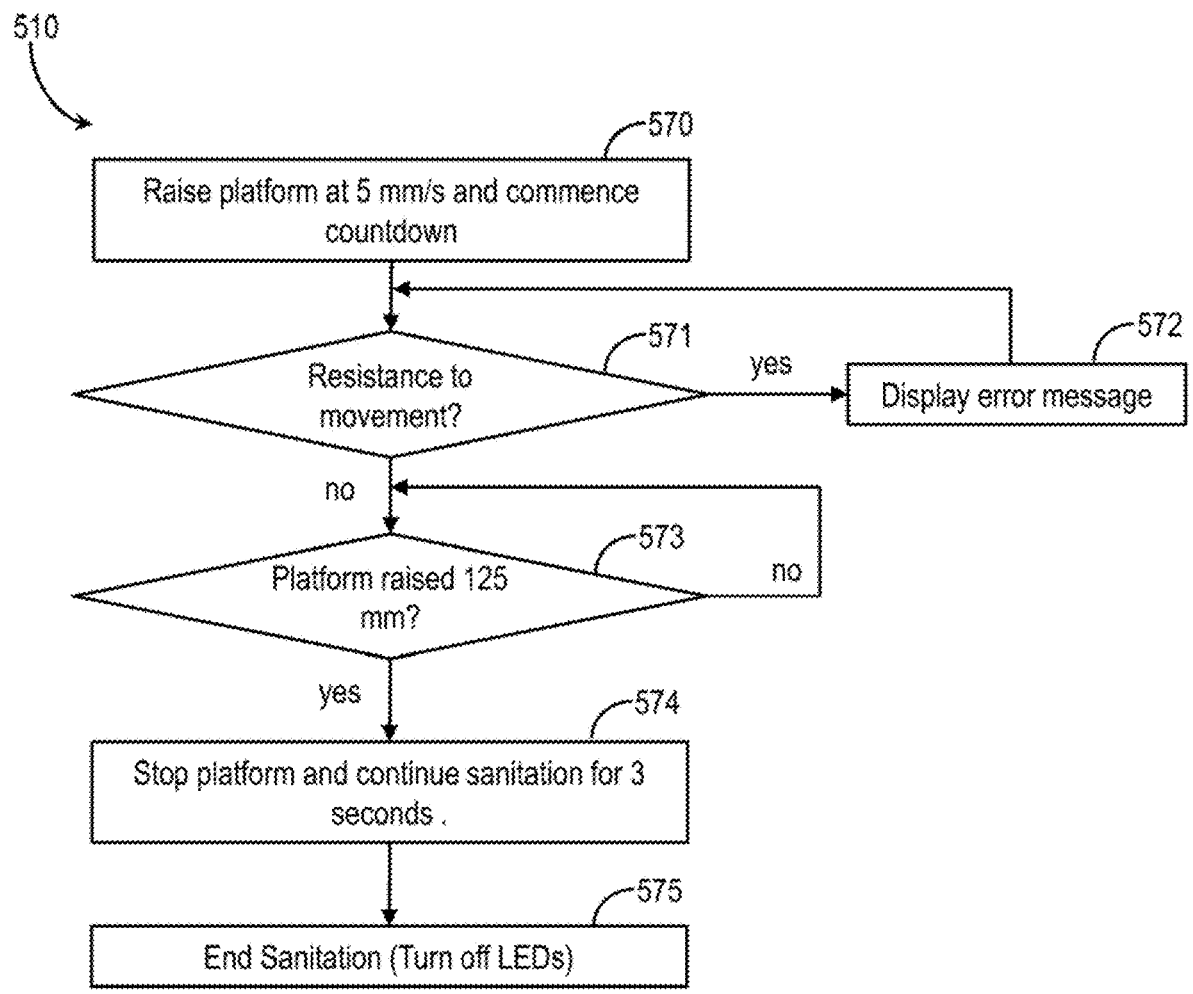
FIG. 5E is a flow chart of a sanitation state, in accordance with an embodiment.

Following the entry state 508, the sanitizer enters a sanitation state 510 (FIG. 5E). During the sanitation state 510, the phone is exposed to high intensity UV-C radiation from the LED printed circuit boards as the platform is raised upward. During the sanitation state, the screen of the sanitizer may display a message, for example, "Sanitizing Phone. Please wash or sanitize your hands."

Figure 5F:
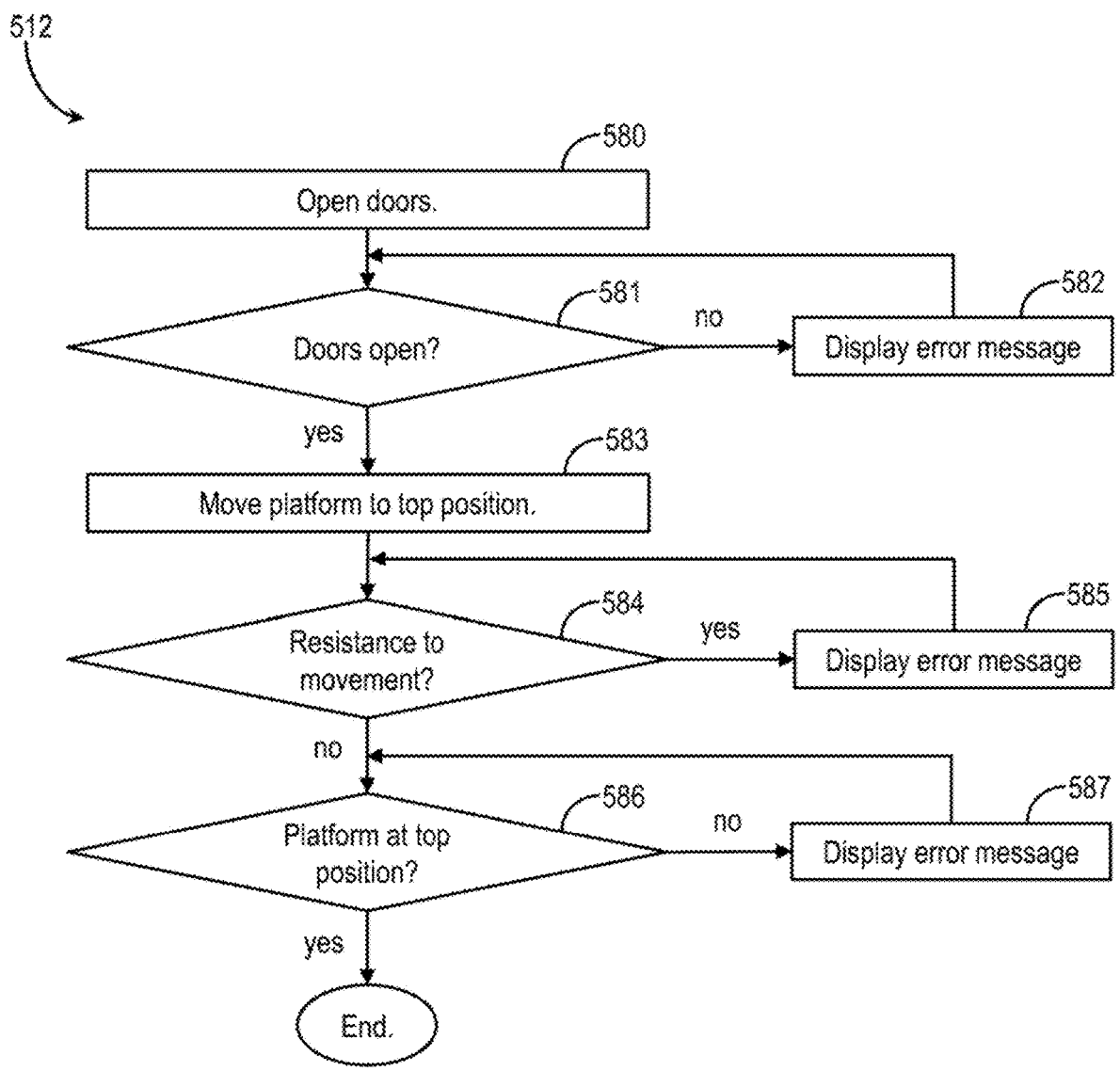
FIG. 5F is a flow chart of an exit state, in accordance with an embodiment.

Following the sanitation state 510, the sanitizer enters an exit state 512 (FIG. 5F). The exit state 512, the doors are opened and the platform and phone are raised upwards out of the chamber for retrieval by the user. During the exit state 512 the screen of the sanitizer may display a message, for example, "Sanitation complete. Please remove your phone". Following the exit state 512, the sanitizer reverts to the ready state 506.

The total duration of the entry state 508, sanitation state 510 and exit state 512 is preferably less than 30 seconds, providing for quick entry, sanitation and retrieval of the phone from the sanitizer. A benefit of the operational modes 500 is they allow for touchless operation of the sanitizer thereby preventing cross contamination between users. A further benefit of the operational modes 500 is the error checking that is performed throughout the initialization sequence 502, the sanitation mode 504 and maintenance mode 514 (see FIGS. 5B-5F), to ensure there is no chance of UV-C radiation escaping the chamber during sanitation, which can be harmful to the user.

Referring now to FIGS. 5B-5C, illustrated therein is a flow chart of the initialization sequence 502.

At 521, the sanitizer determines whether an object (i.e. a mobile phone) is on the platform. The object may be detected by a load sensor (e.g. a micro switch) in the platform.

At 522, if an object is detected, the sanitizer displays an error message and/or error code. The message may be displayed on the screen of the sanitizer. The message may be, for example, "a foreign object has been detected in the device. Please remove object manually using the lever on the side. Please restart device."

At 523, if no object is detected at 522, the actuator moves the platform upward to the highest position. The highest position is when the platform is ~45 mm from the top of the chamber.

At 524, while the platform is in upward motion, the sanitizer determines whether there is resistance to movement of the platform.

At 525, if resistance to movement of the platform is detected (i.e. the platform is unable to move), the sanitizer displays an error message and/or an error code. The message may be, for example, "platform movement cannot be detected. Please ensure nothing is blocking the movement of internal components and restart the device."

At 526, if there is no resistance to movement detected at 528, the sanitizer determines whether the platform is at the highest position. The position of the platform may be detected by, for example, a limit switch at the highest position.

At 527, if the platform is not at the highest position, the sanitizer displays an error message and/or an error code. The message may be, for example: "Unable to complete initialization. Please restart the device."

At 528, when the platform is at the highest position, the actuator moves the platform downward to the lowest position.

At 529, while the platform is in downward motion, the sanitizer determines whether there is resistance to movement of the platform.

At 530, if resistance to movement of the platform is detected (i.e. the platform is unable to move), the sanitizer displays an error message and/or an error code. The message may be the same as the message displayed at 530.

At 531, if there is no resistance to movement detected at 538, the sanitizer determines whether the platform is at the lowest position. The position of the platform may be detected by a limit switch at the lowest position.

At 532, if the platform is not at the lowest position, the sanitizer displays an error message and/or an error code. The message may be the same as the message displayed at 534.

At 533, when the platform is at the lowest position, the doors are opened.

At 534, the sanitizer determines whether the doors have fully opened. The opening of the doors may be detected by a limit switch positioned adjacent to the doors.

At 535, if the doors are not fully open, the sanitizer displays an error message and/or an error code. The error message may be, for example: "Unable to open or close the door. Please ensure doors are not blocked. Object to be sanitized may need to be rotated or centered."

At 536, if the doors are fully open, the sanitizer closes the doors.

At 537, the sanitizer determines whether the doors have fully closed. The closing of the doors may be detected by a limit switch positioned adjacent to the doors.

At 538, if the doors are not fully closed, the sanitizer displays an error message and/or an error code. The error message may be the same as the message at 550.

At 539, if the doors are fully closed, the sanitizer turns on the UV-C LEDs for sixty seconds to sanitize the chamber of the sanitizer. Following sanitization, the LEDs are switched off.

At 540, the actuator moves the platform to the highest position.

At 541, while the platform is in upward motion, the sanitizer determines whether there is resistance to movement of the platform.

At 542, if resistance to movement of the platform is detected (i.e. the platform is unable to move), the sanitizer displays an error message and/or an error code. The message may be the same as the message at 530.

At 543, if there is no resistance to movement detected at 562, the sanitizer determines whether the platform has reached the highest position. The position of the platform may be detected by, for example, a limit switch at the highest position.

At 544, if the platform is not at the highest position, the sanitizer displays an error message and/or an error code. The message may be the same as the message at 534.

At 545, when the platform is at the highest position, the doors are opened.

At 546, the sanitizer determines whether the doors have fully opened. The opening of the doors may be detected by a limit switch positioned adjacent to the doors.

At 547, if the doors are not fully open, the sanitizer displays an error message and/or an error code. The error message may be the same as the message at 550.

If, at 546, the sanitizer determines that the doors are fully open, the initialization sequence 502 ends.

Following each of act 525, 527, 530, 532, 535, 538, 542, 544, 547, wherein the sanitizer displays an error message, the preceding step is performed every ten seconds, up to five times in total, until the outcome is not erroneous. For example, following displaying the error message at 525, act 524 is performed up to five times until there is no resistance to movement detected and the initialization sequence 502 proceeds to 526. If the outcome is still erroneous after five attempts, the sanitizer switches off automatically to prevent unsafe operation.

Referring to FIG. 5D, illustrated therein is a flow chart of the entry state 508.

At 550, the sanitizer determines if there is a phone on the platform. The phone may be detected by a load sensor (e.g. a micro switch) in the platform that is depressed when the phone is placed on the platform by the user.

At 551, when a phone is on the platform, the actuator moves the platform downward to the lowest position (note: the platform is already at the highest position from the ready state 506). The time taken between Acts 550 and 551 should be minimal (no more than 3 seconds) but allowing the sensor sufficient time to detect the presence of the phone on the platform.

At 552, while the platform is in downward motion, the sanitizer determines whether there is resistance to movement of the platform.

At 553, if resistance to movement of the platform is detected (i.e. the platform is unable to move), the sanitizer displays an error message and/or an error code.

At 554, the sanitizer determines whether the platform has descended at least a minimum distance (ex. 120 mm) downward. This minimum distance corresponds to the largest phone width that the sanitizer is able to accommodate. Thus, when the platform has travelled at least 120 mm downward, the entirety of the phone should be within the chamber.

At 555, if the platform has descended at least 120 mm, the doors close.

At 556, the sanitizer determines whether the doors have fully closed. The closing of the doors may be detected by a limit switch positioned adjacent to the doors.

At 557, if the doors are not fully closed, the sanitizer displays an error message and/or an error code.

At 558, once the doors are fully closed, the UV-C LEDs are switched on and sanitation commences. Sanitation commences while the platform is still travelling downward. At least a portion of the phone is sanitized while the platform is travelling downward.

At 559, the sanitizer determines whether the platform is at the lowest position. The position of the platform may be detected by a limit switch at the lowest position. It is necessary for the platform to travel to the lowest position, to ensure that the entirety of the phone is below the LED printed circuit boards, so that the external surfaces of the phone may be exposed to UV-C radiation from the LED printed circuit boards when the platform is raised.

At 560, if the platform is not at the lowest position, the sanitizer displays an error message and/or an error code.

Following each of acts 553, 557 and 560 wherein the sanitizer displays an error message, the preceding step is performed every ten seconds, up to five times in total, until the outcome is not erroneous. For example, following displaying the error message at 553, act 552 is performed up to five times until there is no resistance to movement detected and the entry state 508 proceeds to 554. If the outcome is still erroneous after five attempts, the sanitizer switches off automatically to prevent unsafe operation.

Referring to FIG. 5E, illustrated therein is a flow chart of the sanitation state 510.

At 570, the actuator moves the platform upward to the highest position. The platform is raised at ~5 mm/s upwards to ensure the phone is subjected to the required dose of UV-C radiation (~12 mJ/cm$^2$). Concurrently, a countdown timer is displayed on the screen of the sanitizer. The countdown timer displays the time remaining until the sanitation state 510 is complete. The countdown starts when the platform commences upward travel.

At 571, while the platform is in upward motion, the sanitizer determines whether there is resistance to movement of the platform.

At 572, if resistance to movement of the platform is detected (i.e. the platform is unable to move), the sanitizer displays an error message and/or an error code. Following act 572, act 571 is performed up to five times until there is no resistance to movement detected and the sanitation state 510 proceeds to 573. If there is still resistance to movement of the platform after five attempts, the sanitizer switches off automatically to prevent unsafe operation.

At 573, the sanitizer determines whether the platform has travelled at least 125 mm upward. This distance corresponds to the approximate position of the platform at the time the doors of the sanitizer closed during the entry state (i.e. 555 in FIG. 5D).

At 574, the platform is stopped for 3 seconds and sanitation is continued. This allows for the end of the phone that is in contact with the platform to receive the required dose of UV-C radiation (since the end of the phone in contact with the platform may not have been exposed to any UV-C radiation on the downward travel of the platform between acts 558 and 559 in FIG. 5D).

At 575, the UV-C LEDs are switched off and sanitation is ended. The LED lights switching off coincide with the countdown timer reaching zero (0).

Referring to FIG. 5F, illustrated therein is a flow chart of the exit state 512.

At 580, the doors of the sanitizer are opened.

At 581, the sanitizer determines whether the doors have fully opened. The opening of the doors may be detected by a limit switch positioned adjacent to the doors.

At 582, if the doors are not fully open, the sanitizer displays an error message and/or an error code.

At 583, the actuator moves the platform to the highest position (i.e. ~45 mm from the top of the chamber). Preferably, the platform should move upward quickly (i.e. faster than downward travel or upward travel during the sanitation state) to return to phone to the user as quickly as possible following sanitation.

At 584, while the platform is in upward motion, the sanitizer determines whether there is resistance to movement of the platform.

At 585, if resistance to movement of the platform is detected (i.e. the platform is unable to move), the sanitizer displays an error message and/or an error code.

At 586, if there is no resistance to movement detected at 584, the sanitizer determines whether the platform has is the highest position. The position of the platform may be detected by, for example, a limit switch at the highest position.

At 587, if the platform is not at the highest position, the sanitizer displays an error message and/or an error code.

If at 586, the platform is at the highest position and the exit state 512 ends.

Following each of acts 582, 585 and 587 wherein the sanitizer displays an error message, the preceding step is performed every ten seconds, up to five times in total, until the outcome is not erroneous. For example, following displaying the error message at 582, act 581 is performed up to five times until the doors open and the exit state 512 proceeds to 583. If the outcome is still erroneous after five attempts, the sanitizer switches off automatically to prevent unsafe operation.

Referring back to FIG. 5A, to enter the maintenance mode 514, the sanitizer may require user input, for example, by pressing a key fob to a detector in the sanitizer until the maintenance mode 514 is triggered. When maintenance mode 514 is entered, the screen of the sanitizer may display a message, for example, "Device in maintenance mode."

During the entry state 516, the platform is moved to the lowest position with appropriate error checking until the lowest position is reached (i.e. acts 528, 529, 530, 531, 532 in FIG. 5B). The platform is lowered to expose as much of the interior of the chamber as possible for cleaning. Note, the doors will already be open following the initialization sequence 502.

Following the entry state 516, the sanitizer enters a wait state 518. During the wait state 518, a user (i.e. cleaning staff) may sanitize the interior of the chamber with appropriate cleaning reagents. During the wait state 518, the screen of the sanitizer may display the number of sanitation cycles which may be an indicator of the effective remaining lifetime of the UV-C LEDs.

Following cleaning of the chamber, to enter the exit state 520, the user presses the key fob against the detector of the sanitizer until the exit state 520 is triggered. Following the exit state 520, the initialization sequence 502 is performed.

The sanitizer may be further configured for persisted behavior logging. For example, the date and time of completed sanitation mode 504 cycles, maintenance mode 514 cycles and self-sanitation cycles performed during the initialization sequence 502.

While the above description provides examples of one or more apparatus, methods, or systems, it will be appreciated that other apparatus, methods, or systems may be within the scope of the claims as interpreted by one of skill in the art.

The invention claimed is:

1. A touchless sanitizer for handheld objects, the sanitizer comprising:
    a housing having an opening;
    a chamber, within the housing, for receiving an object to be sanitized, wherein the chamber is adjacent to the opening;
    a platform for moving the object within the chamber, wherein the platform is movable within the chamber between a first position and a second position;
    at least one door for covering the opening and preventing UV radiation from escaping the chamber, wherein the door is moveable between an open position and a closed position;
    one or more ultraviolet radiation sources positioned around the chamber, whereby at least a portion of the chamber can be directly irradiated by the ultraviolet radiation sources;
    an actuator connected to the platform, for moving the platform between the first position and the second position; and
    a detector for receiving a touchless signal prior to receiving the object fully into the chamber, wherein based upon the touchless signal that is received, for a sanitation mode the door is moved to the closed position after moving the platform toward the second position and receiving the object fully into the chamber for sanitation, and for a maintenance mode the door is moved to the open position after moving the platform toward the second position for maintenance of the sanitizer.

2. The sanitizer of claim 1, wherein at least a portion of the chamber and the platform are constructed of a material transmissive to UV radiation.

3. The sanitizer of claim 2, wherein the material is quartz glass.

4. The sanitizer of claim 1, wherein the ultraviolet radiation sources are ultraviolet lamps or LEDs.

5. The sanitizer of claim 1, wherein the door forms an end of the platform.

6. The sanitizer of claim 1, wherein when the platform includes a load sensor for detecting when the object is on the platform.

7. The sanitizer of claim 6, wherein movement of the door from the open to the closed position, and movement of the platform from the second position to the first position is coupled to detecting when the object is on the platform.

8. The sanitizer of claim 1, wherein the detector is disposed on an external surface of the sanitizer.

9. The sanitizer of claim 1, wherein the touchless signal is one of:
    an infrared signal;
    a thermal infrared signal;
    a load signal;
    a proximity signal;
    a radio frequency identification (RFID) signal; or
    a near field communication (NFC) signal.

10. The sanitizer of claim 1, wherein the detector is one of:
    an infrared sensor;
    a thermal infrared sensor;
    a load sensor;
    a proximity sensor;
    a radio frequency identification (RFID) receiver; or
    a near field communication (NFC) receiver.

11. The sanitizer of claim 1, wherein the door being in the open position is mechanically coupled to the platform being in the second position.

12. The sanitizer of claim 1, wherein the door being in the closed position is mechanically coupled to the platform being in the first position.

13. The sanitizer of claim 1, wherein the housing includes an interior reflective to ultraviolet radiation.

14. The sanitizer of claim 1, wherein at least a portion of the chamber is reflective to UV-C radiation.

15. The sanitizer of claim 1, further comprising a display for presenting content including: user instructions, warnings, device status, error messages and advertisements.

* * * * *